United States Patent
Takeda et al.

(10) Patent No.: US 9,398,896 B2
(45) Date of Patent: Jul. 26, 2016

(54) ULTRASOUND DIAGNOSTIC IMAGING APPARATUS

(71) Applicants: Yoshihiro Takeda, Hachioji (JP); Daisuke Kaji, Hachioji (JP)

(72) Inventors: Yoshihiro Takeda, Hachioji (JP); Daisuke Kaji, Hachioji (JP)

(73) Assignee: KONICA MINOLTA MEDICAL & GRAPHIC, INC., Tokyo (JP)

(*) Notice: Subject to any disclaimer, the term of this patent is extended or adjusted under 35 U.S.C. 154(b) by 120 days.

(21) Appl. No.: 13/688,649

(22) Filed: Nov. 29, 2012

(65) Prior Publication Data

US 2013/0137986 A1 May 30, 2013

(30) Foreign Application Priority Data

Nov. 30, 2011 (JP) .................................. 2011-261099

(51) Int. Cl.
| | |
|---|---|
| *A61B 8/14* | (2006.01) |
| *A61B 8/08* | (2006.01) |
| *G01S 15/89* | (2006.01) |
| *G01S 7/52* | (2006.01) |

(52) U.S. Cl.
CPC ............... *A61B 8/145* (2013.01); *A61B 8/5207* (2013.01); *G01S 7/5202* (2013.01); *G01S 7/52038* (2013.01); *G01S 15/895* (2013.01); *G01S 15/8963* (2013.01)

(58) Field of Classification Search
None
See application file for complete search history.

(56) References Cited

U.S. PATENT DOCUMENTS

| | | | | |
|---|---|---|---|---|
| 6,113,545 | A * | 9/2000 | Chiao et al. | 600/447 |
| 6,213,947 | B1 * | 4/2001 | Phillips | 600/443 |
| 7,273,455 | B2 * | 9/2007 | Angelsen et al. | 600/437 |
| 7,682,309 | B2 * | 3/2010 | Ji et al. | 600/437 |
| 8,388,536 | B2 * | 3/2013 | Azuma | G01S 7/52022 600/458 |
| 2004/0249283 | A1 * | 12/2004 | Kantorovich et al. | 600/442 |
| 2010/0036255 | A1 * | 2/2010 | Itani | G01S 7/52038 600/458 |
| 2013/0116557 | A1 * | 5/2013 | Yoshikawa | 600/431 |
| 2014/0180097 | A1 * | 6/2014 | Rothberg et al. | 600/438 |
| 2014/0288429 | A1 * | 9/2014 | Taniguchi | 600/447 |

FOREIGN PATENT DOCUMENTS

| | | |
|---|---|---|
| JP | 2004-298620 A | 10/2004 |
| JP | 2008-043721 A | 2/2008 |

* cited by examiner

*Primary Examiner* — Long V Le
*Assistant Examiner* — Kevin Pontius
(74) *Attorney, Agent, or Firm* — Holtz, Holtz & Volek PC

(57) ABSTRACT

Disclosed is an ultrasound diagnostic imaging apparatus including an ultrasound probe which outputs a transmission ultrasound wave toward a subject due to a driving signal and which outputs a received signal by receiving a reflection ultrasound wave from the subject, a transmitting unit which makes the ultrasound probe generate the transmission ultrasound wave by outputting each of a first transmission signal, a second transmission signal, a third transmission signal and a fourth transmission signal as the driving signal, and a signal component extraction unit which extracts a higher harmonic component and a difference frequency component by compounding a first received signal, a second received signal, a third received signal and a fourth received signal.

4 Claims, 19 Drawing Sheets

*FIG.19*
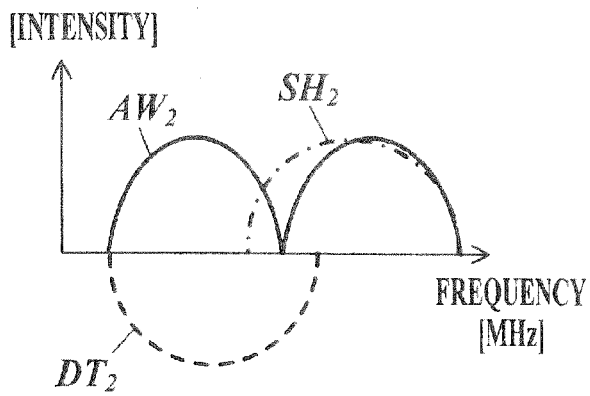
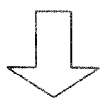
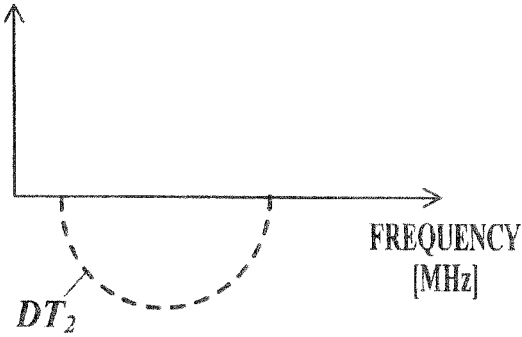
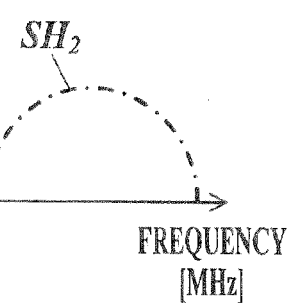
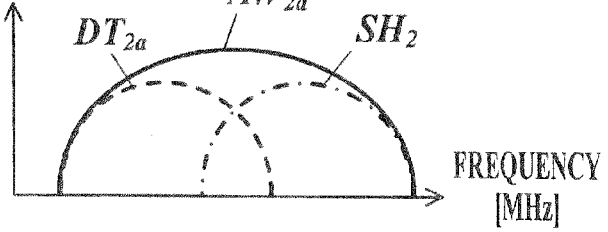

ULTRASOUND DIAGNOSTIC IMAGING APPARATUS

BACKGROUND OF THE INVENTION

1. Field of the Invention

The present invention relates to an ultrasound diagnostic imaging apparatus.

2. Description of Related Art

Ultrasound diagnostic imaging apparatus is a medical imaging device which obtains tomographic images of soft tissues inside a subject from its body surface in a minimally invasive way by performing the ultrasound pulse echo technique. Such ultrasound diagnostic imaging apparatus has number of characteristics such as smaller in size, lower in cost and safer due to no exposure to radiation such as X-rays comparing to other medical imaging devices and such as blood flow imaging is possible by applying the Doppler effect. Therefore, such ultrasound diagnostic imaging apparatus has been used widely in the fields of circulatory system (coronary artery of heart), digestive system (stomach and intestines), internal medicine system (live, pancreas, spleen), urinary system (kidney, bladder), obstetrics and gynecology system and such like.

Moreover, in recent years, harmonic imaging (HI) diagnosis using harmonic component and not conventional fundamental component of ultrasound is performed in order to improve accuracy of diagnosis using ultrasound images. Harmonic component is a frequency component which is generated by the fundamental component to be transmitted being affected by nonlinearity of inside a subject. Because clear diagnostic images which cannot be obtained by the conventional B-mode diagnosis using fundamental component can be obtained, HI diagnosis is becoming the normal diagnosis modality.

The ultrasound images obtained by HI diagnosis have advantages such as improvement in contract resolution due to having high S/N because their sidelobe level is small and improvement in azimuth resolution due to narrow beam width comparing to ultrasound images of fundamental component. Further, there are number of advantages such that multiple reflections do not occur because sound pressure is small in short distance and fluctuation of sound pressure is small, that degradation beyond focus is about the same as in fundamental component and that great invasion depth can be obtained in harmonic component comparing to fundamental component of same frequency.

Although ultrasound diagnostic imaging using harmonic component has number of advantages as described above, there is a problem that distance resolution does not improves because the frequency band of ultrasound wave by which sending and receiving is carried out is limited to the frequency band defined by the characteristic of the ultrasound probe to be used.

In view of the above problem, JP 2004-298620 discloses performing phase adjustment of waveform with respect to two fundamental waves having difference frequencies to transmit and receive ultrasound wave and obtaining harmonic component of broadband by using a difference frequency component obtained from the received two fundamental components in a conventional ultrasound diagnostic imaging apparatus.

Moreover, JP 2008-43721 discloses transmitting ultrasound wave by a transmission signal having a waveform of broadband where the phase is adjusted and obtaining harmonic component of broadband by using the base-band harmonic component obtained by receiving the ultrasound wave.

SUMMARY OF THE INVENTION

However, it is necessary to generate a transmission signal having a particular waveform where the phase is adjusted in the techniques described in the above patent documents. Therefore, a special transmission circuit configuration is needed and the cost increases due to the circuit becoming large in its scale.

Moreover, there is known an ultrasound diagnostic imaging apparatus utilizing a transmission circuit which generates a square waveform to be applied as a general transmission signal. However, in such ultrasound diagnosis imaging apparatus, although a plurality of frequencies can be included in a transmission signal and transmission ultrasound wave of a broadband signal waveform can be output, it is difficult to perform phase adjustment arbitrarily and harmonic component of broadband cannot be obtained easily.

Further, even if a transmission signal which is adjusted to have a desired waveform can be generated by the techniques described in JP 2004-298620 and JP2008-43721, phase of the ultrasound wave obtained by adjusting the transmission signal may be destroyed during transmission due to unevenness of the medium through which ultrasound wave transmits, beam forming and the like and such condition cannot be adjusted in the techniques described in JP 2004-298620 and JP2008-43721. Therefore, there are cases where good ultrasound images cannot be obtained.

The present invention was made in view of the above problems and an object of the present invention is to provide an ultrasound diagnostic imaging apparatus which can obtain a broadband harmonic component by a transmission signal which can output transmission ultrasound wave with a simple configuration and obtain a good ultrasound image.

In order to achieve the above object, an ultrasound diagnostic imaging apparatus reflecting one aspect of the present invention includes an ultrasound probe which outputs a transmission ultrasound wave toward a subject due to a driving signal and which outputs a received signal by receiving a reflection ultrasound wave from the subject, a transmitting unit which makes the ultrasound probe generate the transmission ultrasound wave by outputting each of a first transmission signal, a second transmission signal which is a phase-inverted version of a signal waveform of the first transmission signal, a third transmission signal is a time-inverted version of the signal waveform of the first transmission signal and a fourth transmission signal which is a phase-inverted and time-inverted version of the signal waveform of the first transmission signal as the driving signal, the waveform of the first transmission signal being different from waveforms of the third transmission signal and the fourth transmission signal, and a signal component extraction unit which extracts a higher harmonic component and a difference frequency component by compounding a first received signal obtained from a reflection ultrasound wave corresponding to the transmission ultrasound wave output from the ultrasound probe due to the first transmission signal, a second received signal obtained from a reflection ultrasound wave corresponding to the transmission ultrasound wave output from the ultrasound probe due to the second transmission signal, a third received signal obtained from a reflection ultrasound wave corresponding to the transmission ultrasound wave output from the ultrasound prove due to the third transmission signal and a fourth received signal obtained from a reflection ultrasound wave corresponding to the transmission ultrasound wave output from the ultrasound probe due to the fourth transmission signal.

Preferably, the ultrasound diagnosis imaging apparatus further includes a phase changing unit which changes a relative phase relation between the higher harmonic component and the difference frequency component extracted by the signal component extraction unit, a signal compounding unit which compounds the higher harmonic component and the difference frequency component wherein the relative phase relation is changed by the phase changing unit, and an image generation unit which generates ultrasound image data of inside the subject on the basis of a received signal compounded by the signal compounding unit.

Preferably, the phase changing unit sets a changing amount of the relative phase relation between the higher harmonic component and the difference frequency component according to a depth of the reflection ultrasound wave which is received by the ultrasound probe.

Preferably, an image generation unit which converts each of the higher harmonic component and the difference frequency component extracted by the signal component extraction unit into brightness data in which intensity of a signal is indicated in terms of a brightness of an image and generates ultrasound image data of inside the subject by compounding the brightness data obtained by converting the high harmonic component and the brightness data obtained by converting the difference frequency component.

Preferably, the higher harmonic component is a second harmonic component.

Preferably, the signal component extraction unit extracts the second harmonic component by obtaining a sum of the first received signal, the second received signal, the third received signal and the fourth received signal and extracts the difference frequency component by obtaining a difference between a sum of the first received signal and the second received signal and a sum of the third received signal and the fourth received signal.

Preferably, the transmitting unit outputs the driving signal in a form of a pulse signal of a square wave.

BRIEF DESCRIPTION OF THE DRAWINGS

The present invention will become more fully understood from the detailed description given hereinbelow and the appended drawings which are given by way of illustration only, and thus are not intended as a definition of the limits of the present invention, and wherein:

FIG. 19 is a diagram for explaining a procedure of phase adjustment of harmonic components;

DESCRIPTION OF THE PREFERRED EMBODIMENTS

Figure 1:
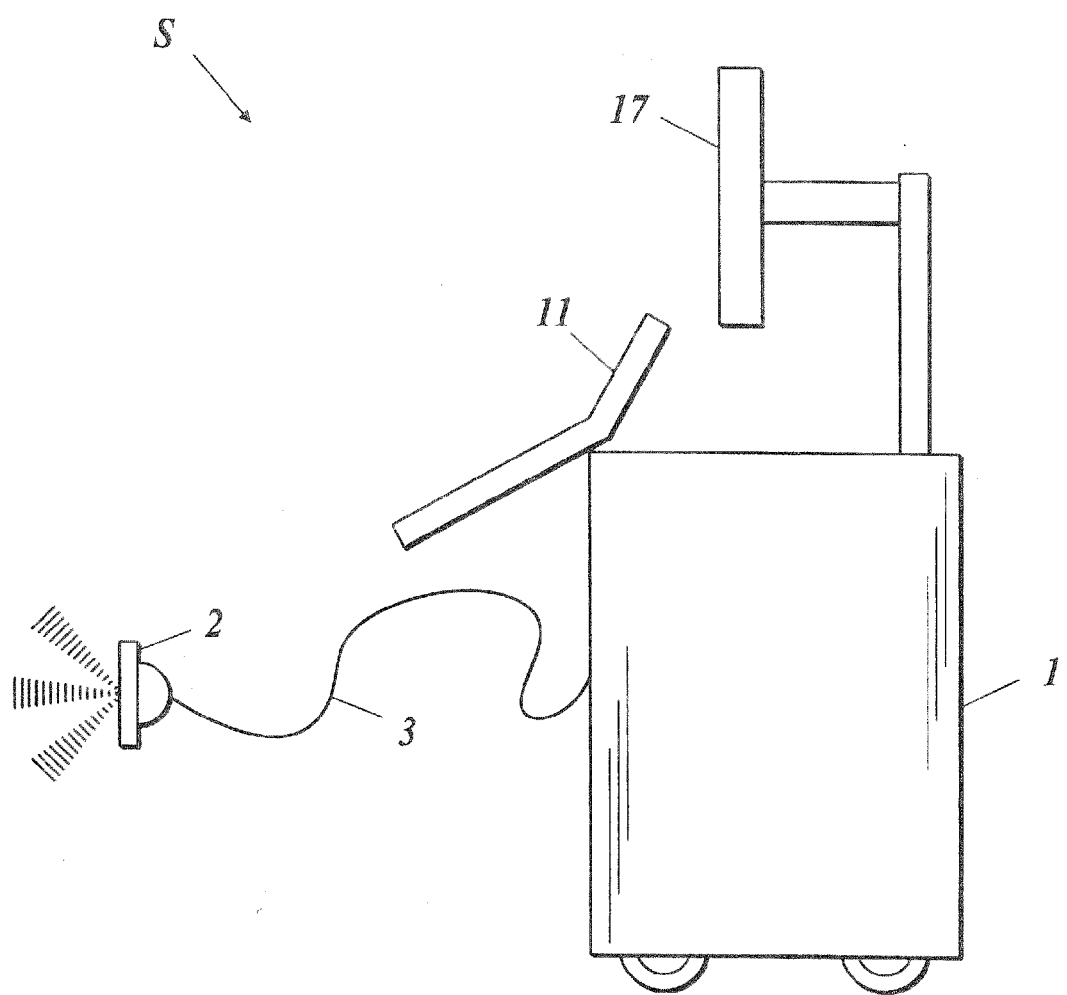
FIG. 1 is a diagram showing an outer configuration of an ultrasound diagnostic imaging apparatus.

Hereinafter, an ultrasound diagnostic imaging apparatus according to embodiments of the present invention will be described with reference to the drawings. However, the scope of the invention is not limited to the examples shown in the drawings. In the following descriptions, same references are used for same functions and configurations and their descriptions are omitted.

(First Embodiment)

Figure 2:
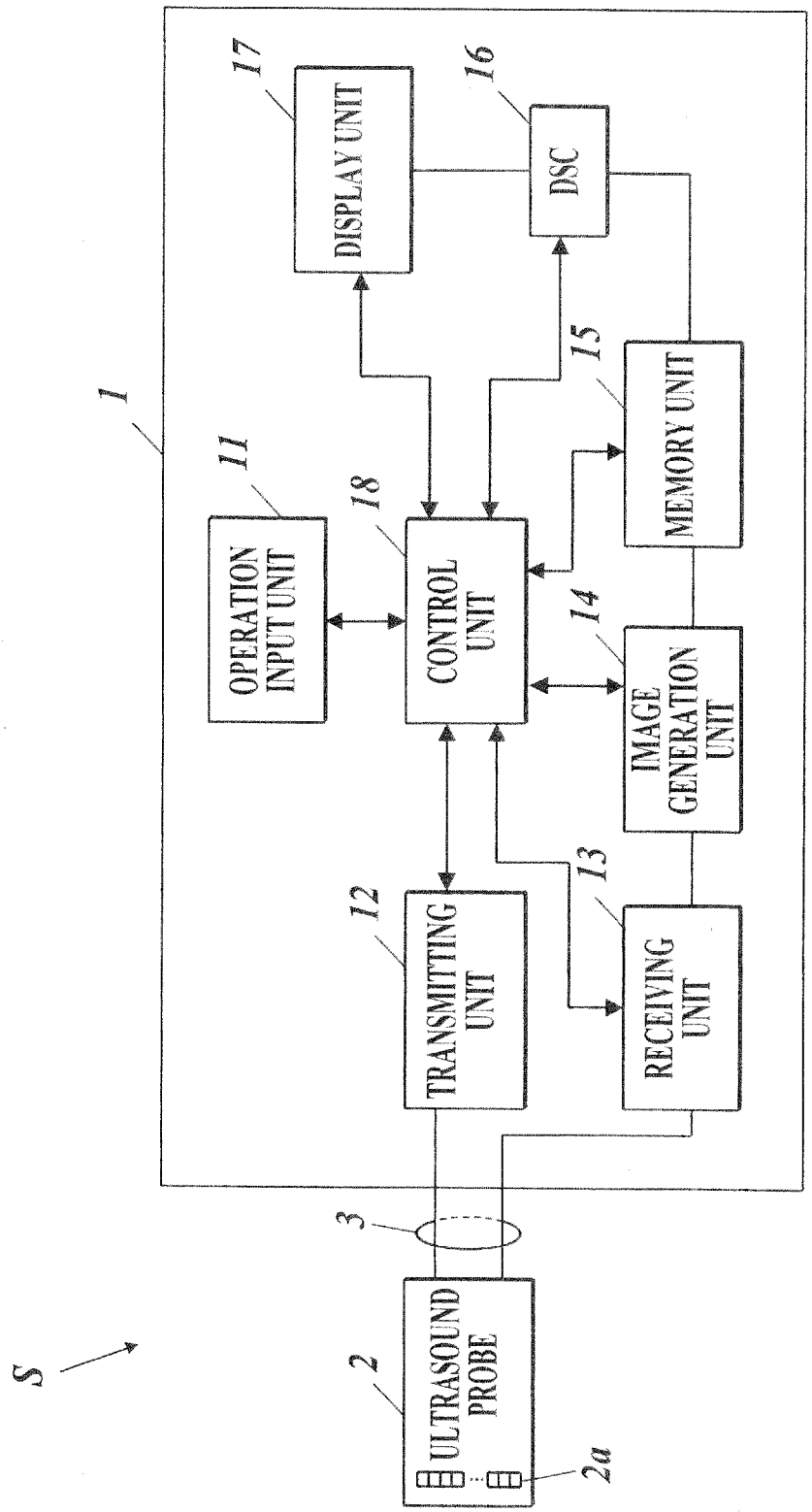
FIG. 2 is a block diagram showing a schematic configuration of the ultrasound diagnostic imaging apparatus.

As shown in FIGS. 1 and 2, the ultrasound diagnostic imaging apparatus S according to the first embodiment includes an ultrasound diagnostic imaging apparatus main body 1 and an ultrasound probe 2. The ultrasound probe 2 transmits ultrasound wave (transmission ultrasound wave)

toward a subject such as a living matter (omitted in the drawing) and also receives reflection wave (reflection ultrasound wave: echo) of ultrasound wave which reflected off the subject. The ultrasound diagnostic imaging apparatus main body 1 is connected with the ultrasound probe 2 via a cable 3, and the ultrasound diagnostic imaging apparatus main body 1 transmits a driving signal which is an electric signal to the ultrasound probe 2 to make the ultrasound probe 2 transmit transmission ultrasound wave toward the subject and also forms an image of the internal condition of the subject as an ultrasound image on the basis of a received signal which is an electric signal generated in the ultrasound probe 2 according to the reflection ultrasound wave from inside the subject received by the ultrasound probe 2.

The ultrasound probe 2 includes transducers 2a formed of piezo-electric devices, and the plurality of transducers 2a are arranged in one dimensional array in an orientation direction, for example. In the embodiment, for example, an ultrasound probe 2 having 192 transducers 2a is used. Here, the transducers 2a may be arranged in two dimensional array. Further, the number of transducers 2a can be set arbitrarily. In the embodiment, a linear scanning type electronic scanning probe is used as the ultrasound probe 2. However, any of an electronic scanning type and a mechanical scanning type can be used. Further, any of a linear scanning type, a sector scanning type and a convex scanning type can be used.

As shown in FIG. 2, the ultrasound diagnostic imaging apparatus main body 1 includes an operation input unit 11, a transmitting unit 12, a receiving unit 13, an image generation unit 14, a memory unit 15, a DSC (Digital Scan Converter) 16, a display unit 17 and a control unit 18, for example.

The operation input unit 11 includes various types of switches, buttons, a track-ball, a mouse, a key board and the like for inputting a command for instructing start of diagnosis and data such as personal information of a subject, and the operation input unit 11 outputs operation signals to the control unit 18.

Figure 3:
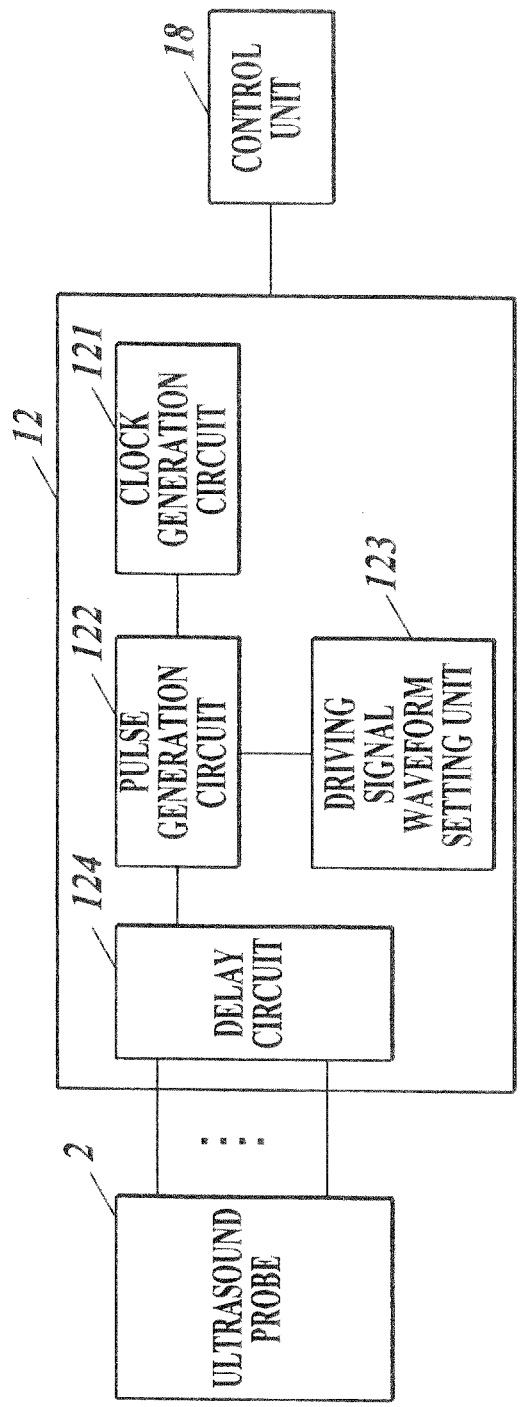
FIG. 3 is a block diagram showing a schematic configuration of a transmitting unit.

The transmitting unit 12 is a circuit to make the ultrasound probe 2 generate transmission ultrasound waves by supplying driving signals which are electronic signals to the ultrasound probe 2 via the cable 3 in compliance with the control of the control unit 18. More specifically, as shown in FIG. 3, the transmitting unit 12 includes a clock generating circuit 121, a pulse generating circuit 122, a driving signal waveform setting unit 123 and a delay circuit 124, for example.

The clock generating circuit 121 is a circuit for generating clock signals which decide transmission timing and transmission frequency of driving signals.

The pulse generating circuit 122 is a circuit for generating pulse signals as driving signals in predetermined cycles. The pulse generating circuit 122 can generate pulse signals of square wave by switching ternary voltage. At this time, amplitude of a pulse signal is set so that positive polarity and negative polarity be the same. However, this is not limitative in any way. Pulse signals may be generated by switching binary voltage. Further, signal to be generated is not limited to the pulse signal of square wave and a signal of other waveform such as sine wave may be generated, for example.

The driving signal waveform setting unit 123 sets the waveform of driving signal by setting the duty ratio of a pulse signal to be output from the pulse generation circuit 122. That is, the pulse generation circuit 122 outputs a pulse signal having pulse waveform according to the duty ratio set by the driving signal waveform setting unit 123. Here, duty ratio can be changed by an input operation performed on the operation input unit 11 to be set, for example. Further, configuration may be such that by identifying the ultrasound probe 2 which is connected to the ultrasound diagnostic imaging apparatus main body 1, the duty ratio corresponding to the identified ultrasound probe 2 is set. Details of setting of duty ratio by the driving signal waveform setting unit 123 will be described later.

The delay circuit 124 is a circuit for setting a delay time for each path regarding transmission timing of driving signals, each path corresponding to each transducer, and converging transmission beams formed of transmission ultrasound waves by delaying transmission of driving signals for the set delay time.

The transmitting unit 12 which is configured as described above sequentially switches the plurality of transducers 2a which supply driving signals, shifting by a predetermined numbers for each transmitting and receiving of ultrasound wave in compliance with the control of the control unit 18 and supplies driving signals to the plurality of transducers 2a which are selected to perform output to carry out scanning.

Figure 4:
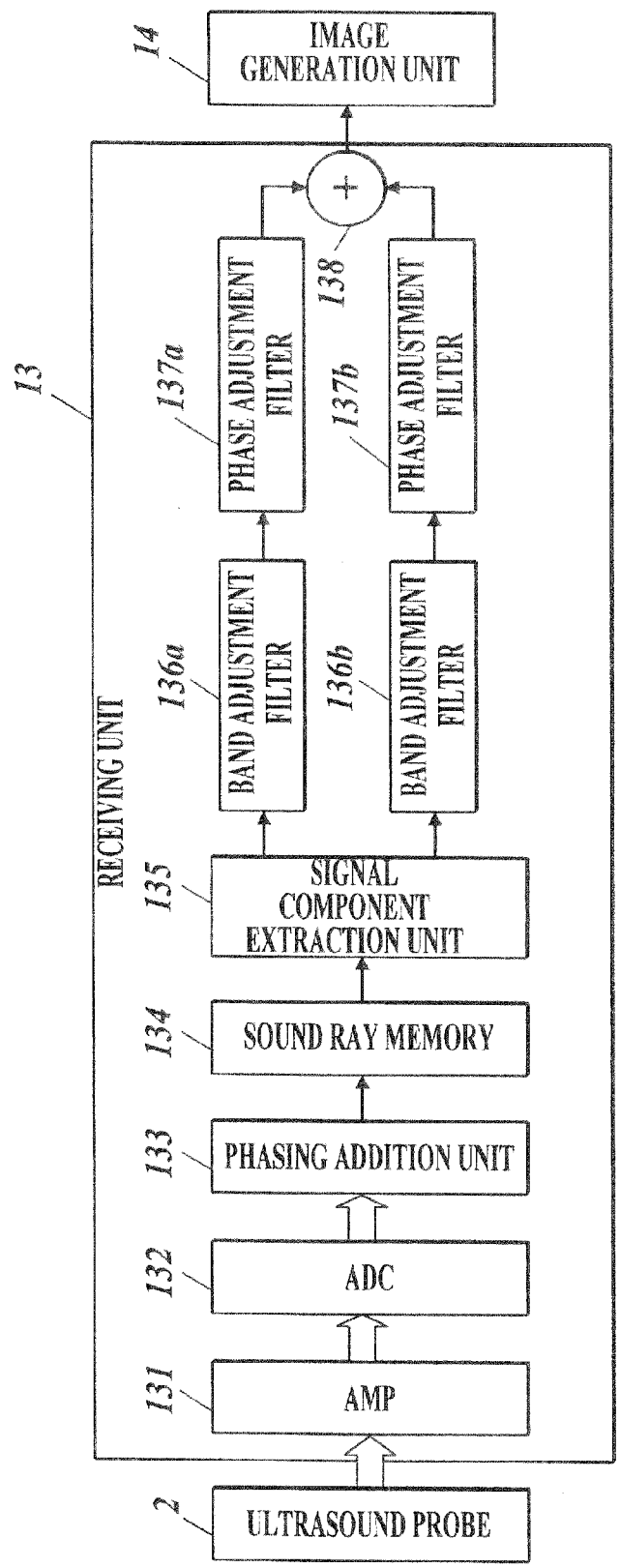
FIG. 4 is a block diagram showing a schematic configuration of a receiving unit.

As shown in FIG. 2, the receiving unit 13 is a circuit which receives a received signal which is an electric signal from the ultrasound probe 2 via the cable 3 according to the control of the control unit 18. As shown in FIG. 4, the receiving unit 13 includes an AMP (amplifier) 131, an ADC (Analog/Digital Converter) 132, a phasing addition unit 133, a sound ray memory 134, a signal component extraction unit 135, band adjustment filters 136a, 136b, phase adjustment filters 137a and 137b and a signal adder 138, for example.

The AMP 131 is a circuit for amplifying the received signal at a predetermined amplifying ratio which is set in advance with respect to each of the individual paths corresponding respectively to the transducers 2a.

The ADC 132 is a circuit for performing analog-digital conversion (A/D conversion) of the amplified received signal.

The phasing addition unit 133 is a circuit for adjusting time phase by applying delay time to each of the individual paths corresponding respectively to the transducers 2a with respect to the received signal on which A/D conversion is performed and for generating sound ray data by adding (phasing addition) the signals. That is, the phasing addition unit 133 generates sound ray data by performing receive beam forming with respect to the received signal of each of the transducers 2a.

The sound ray memory 134 is a memory for temporarily storing the sound ray data generated in the phasing addition unit 133. The sound ray memory 134 can store a plurality of sound ray data each in different region.

The signal component extraction unit 135 reads out a plurality of sound ray data stored in the sound ray memory 134 and adds the read out sound ray data to extract a difference frequency component and a second harmonic component. How the difference component and the second harmonic component are extracted will be described later. The signal component extraction unit 135 outputs the sound ray data from which the second harmonic component is extracted to the band adjustment filter 136a and also outputs the sound ray data from which the difference frequency component is extracted to the band adjustment filter 136b.

The band adjustment filter 136a is a band limiting filter (band pass filter) which performs filter processing on the input sound ray data wherein the filter processing removes signal components outside the frequency band of the second harmonic component. The band adjustment filter 136a outputs the sound ray data on which filter processing is performed to the phase adjustment filter 137a. In the embodiment, configuration may be such that the band adjustment filter 136a is not provided.

The phase adjustment filter 137a is a filter which displaces the phase of the input sound ray data by a predetermined amount and outputs the displaced sound ray data. The displacement amount of the phase of sound ray data can change according to the depth of reflection ultrasound wave to be received, for example, by the instruction from the control unit 18. By having such configuration, band of harmonic component can be broad by adjusting the displacement amount of the phase even when the band of harmonic component does not broaden depending on the depth.

The band adjustment filter 136b is a band limiting filter which performing filter processing on the input sound ray data wherein the filter processing removes signal components outside of the frequency band of the difference frequency component. The band adjustment filter 136b outputs the sound ray data on which the filter processing is performed to the phase adjustment filter 137b. In the embodiment, configuration may be such that the band adjustment filter 136b is not provided.

The phase adjustment filter 137b is a filter which displaces the phase of the input sound ray data by a predetermined amount and outputs the displaced sound ray data. The displacement amount of the phase of the sound ray data can change according to the depth of reflection ultrasound wave to be received, for example, by the instruction of the control unit 18. By having such configuration, band of harmonic component can be broad by adjusting the displacement amount of the phase even when the band of harmonic component does not broaden depending on the depth.

In the embodiment, both the phase adjustment filter 137a for changing the phase of the second harmonic component and the phase adjustment filter 137b for changing the phase of the difference frequency component are provided. However, embodiment may be such that only one of the phase adjustment filter 137a and the phase adjustment filter 137b is provided.

The signal adder 138 generates sound ray data in which the difference frequency component and the second harmonic component are compounded by adding the sound ray data output from the phase adjustment filter 137b and the sound ray data output from the phase adjustment filter 137b and outputs the generated sound ray data to the image generation unit 14.

As described above, the phase adjustment filters 137a and 137b constitute a phase changing unit which changes the relative phase relation between a higher harmonic component and a difference frequency component which are extracted by the signal component extraction unit.

Further, the signal adder 138 constitutes a signal compounding unit which compounds a higher harmonic component and a difference frequency component where the relative phase relation therebetween is changed by the phase changing unit.

Figure 5:
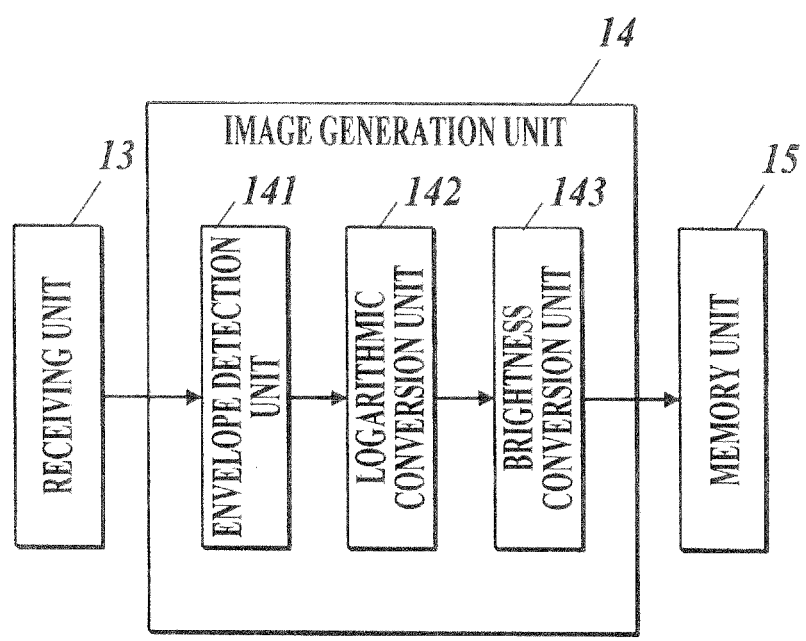
FIG. 5 is a block diagram showing a schematic configuration of an image generation unit.

As shown in FIG. 5, the image generation unit 14 includes an envelope detection unit 141, a logarithmic conversion unit 142 and a brightness conversion unit 143, for example.

The envelope detection unit 141 performs full wave rectification with respect to the input sound ray data and obtains envelope data. The envelope detection unit 141 outputs the obtained envelope data to the logarithmic conversion unit 142.

The logarithmic conversion unit 142 performs logarithmic amplification on the input envelope data. At this time, gain and dynamic range can be adjusted or the like.

The brightness conversion unit 143 generates B-mode image data by performing amplitude/brightness conversion which quantizes the intensity of the signal indicated by the envelope data on which logarithmic amplification is performed into 256 tones. That is, the B-mode image data expresses intensity of the received signal in terms of brightness. The brightness conversion unit 143 outputs the B-mode image data which is generated as described above to the memory unit 15.

As shown in FIG. 2, the memory unit 15 is configured by including a semiconductor memory such as DRAM (Dynamic Random Access Memory), for example, and stores the B-mode image data which is transmitted from the image generation unit 14 frame by frame. That is, the memory unit 15 can store the B-mode image data as ultrasound image data formed in units of frame. The ultrasound image data stored in the memory unit 15 is read out in accordance with the control of the control unit 18 and is transmitted to the DSC 16.

The DSC 16 converts the ultrasound image data which is received from the memory unit 15 into image signal of television signal scan method and outputs the image signal to the display unit 17.

As for the display unit 17, a display apparatus such as LCD (Liquid Crystal Display), a CRT (Cathode-Ray Tube) display, an organic EL (Electronic Luminescence) display, an inorganic EL display, a plasma display and the like can be applied. In the embodiment, a LCD including a back light of white or full-color LED (Light-Emitting Diode) is used as the display unit 17. The display unit 17 displays an ultrasound image in the display screen according to the image signal which is output from the DSC 16. Here, a printing apparatus such as a printer or the like can be used instead of the display apparatus.

The control unit 18 includes a CPU (Central Processing Unit), a ROM (Read Only Memory) and a RAM (Random Access Memory), for example, and the control unit 18 reads out various types of processing programs such as a system program stored in the ROM and expands the programs in the RAM and further, performs central control of an operation of each unit of the ultrasound diagnostic imaging apparatus S in accordance with the expanded programs.

The ROM is configured by including a non-volatile memory or the like such as a semiconductor, and the ROM stores the system program corresponding to the ultrasound diagnostic imaging apparatus S, various types of processing programs which are executable on the system program, various types of data and the like. These programs are stored in the form of program codes which can be read by a computer, and the CPU sequentially executes operations according to the program codes.

The RAM forms a work area where various types of programs which are to be executed by the CPU and data according to the programs are to be stored temporarily.

Next, driving signal which is generated by the transmitting unit 12 of the ultrasound diagnostic imaging apparatus S configured as described above will be described.

In the embodiment, harmonic components of broad band and good quality can be obtained by obtaining sound ray data by performing transmitting and receiving of ultrasound wave for four times in the ultrasound diagnostic imaging apparatus S. More particularly, waveform of a driving signal is set by the driving signal waveform setting unit 123 of the transmitting unit 12 so that the first transmission signal, the second transmission signal which is a phase-inverted version of the signal waveform of the first transmission signal, the third transmission signal which is a time-inverted version of the signal waveform of the first transmission signal and the fourth transmission signal which is a phase-inverted and time-inverted version of the signal waveform of the first transmission signal are generated. Further, by compounding the received signals obtained by transmitting and receiving the first to the fourth transmission signals in the signal component extraction unit 135 and the signal adder 138 of the receiving unit 13, harmonic components of broadband and good quality are obtained.

Figure 6:
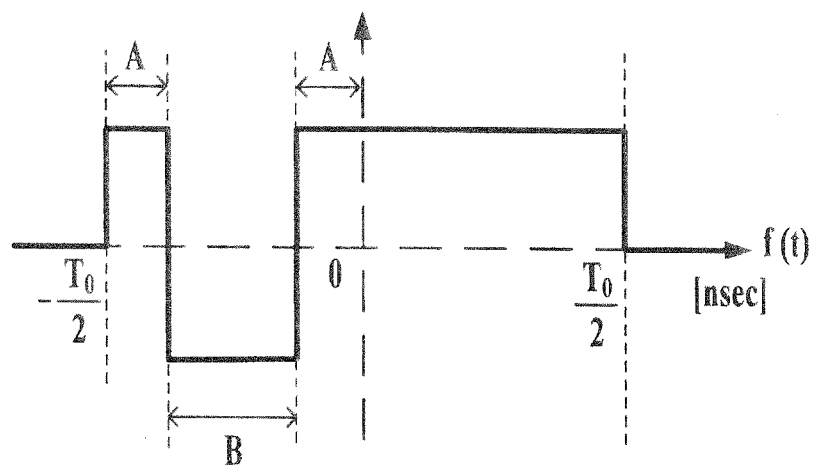
FIG. 6 is a diagram for explaining a waveform of the first transmission signal.

First, the transmitting unit 12 generates the first transmission signal by the driving signal waveform setting unit 123. FIG. 6 shows an example of waveform of the driving signal which is preferred to be applied to the first transmission signal.

That is, the waveform of the first transmission signal shown in FIG. 6 is a square wave wherein one cycle is expressed with the periodic function f(t) of $T_0$ and is expressed as the sum of integer multiplication component of frequency $1/T_0$ by performing the Fourier series expansion by using parameter A and parameter B which define the duty ratio. As shown in FIG. 6, waveform of the first transmission signal formed of a pulse from $-T_0/2$ to $T_0/2$ is set so as to be different from the waveforms of the third transmission signal and the fourth transmission signal. This is because, the higher harmonic component and the difference frequency component cannot be extracted because when the waveform of the first transmission signal and the waveform of the third transmission signal (or the fourth transmission signal) are the same, their corresponding received signals are also the same.

The periodic function f(t) shown in FIG. 6 can be expressed by the following formula (1).

[Numerical formula 1]

$$f(t) = a_0 + \sum_{n=1}^{\infty} \left[ a_n \cos\left\{2\pi\left(\frac{n}{T_0}\right)t\right\} + b_n \sin\left\{2\pi\left(\frac{n}{T_0}\right)t\right\} \right] \quad (1)$$

In the above formula (1), component $a_0$, coefficient $a_n$ and coefficient $b_n$ can be replaced by the formulas shown in the following formulas (2) to (4).

[Numerical formula 2]

$$a_0 = \frac{4A}{T_0} \quad (2)$$

$$a_n = \frac{2}{T_0}\int_{\frac{T_0}{2}}^{\frac{T_0}{2}} f(t)\cos\left\{2\pi\left(\frac{n}{T_0}\right)t\right\} dt = \frac{2}{\pi n}\left[\sin\left(2\pi n\frac{A}{T_0}\right) - \sin\left(\pi n - 2\pi n\frac{A}{T_0}\right)\right] \quad (3)$$

$$b_n = \frac{2}{T_0}\int_{\frac{T_0}{2}}^{\frac{T_0}{2}} f(t)\sin\left\{2\pi\left(\frac{n}{T_0}\right)t\right\} dt = \frac{2}{\pi n}\left[\cos\left(2\pi n\frac{A}{T_0}\right) - \cos\left(\pi n - 2\pi n\frac{A}{T_0}\right)\right] \quad (4)$$

When n=1, coefficient $a_1$ and coefficient $b_1$ are indicated by the following formulas (5) and (6).

[Numeral formula 3]

$$a_1 = 0 \quad (5)$$

$$b_1 = \frac{4}{\pi}\cos\left(2\pi\frac{A}{T_0}\right) \quad (6)$$

Further, when n=2, coefficient $a_2$ and coefficient $b_2$ are indicated by the following formulas (7) and (8).

[Numerical formula 4]

$$a_2 = \frac{2}{\pi}\sin\left(4\pi\frac{A}{T_0}\right) \quad (7)$$

$$b_2 = 0 \quad (8)$$

Here, depending on the band characteristic of the ultrasound probe 2 to be used, the first fundamental component and the second fundamental component which is a frequency component double the first fundamental component become dominant in the component of the waveform of the transmission signal which passes through the ultrasound probe 2. Therefore, the component $a_0$ which is low frequency comparing to the band defined by the band characteristic of the ultrasound probe 2 and frequency components which are three times or more of the first fundamental component can be ignored, and the periodical function f(t) shown in FIG. 6 can be approximately expressed by the following formula (9).

[Numerical formula 5]

$$f(t) \cong b_1\sin\left(\frac{2\pi}{T_0}t\right) + a_2\cos\left(\frac{4\pi}{T_0}t\right) \quad (9)$$

$$= \frac{4}{\pi}\cos\left(2\pi\frac{A}{T_0}\right)\cdot\sin\left(\frac{2\pi}{T_0}t\right) + \frac{2}{\pi}\sin\left(4\pi\frac{A}{T_0}\right)\cdot\cos\left(\frac{4\pi}{T_0}t\right)$$

Therefore, the transmission ultrasound where the first fundamental component and the second fundamental component expressed by the above formula (9) are the main components is output by the ultrasound probe 2.

Here, waveform of the first transmission signal is not limited to what is described above and can be set arbitrarily.

Next, the transmitting unit 12 generates the second transmission signal by the driving signal waveform setting unit 123. The second transmission signal is formed by displacing the phase of the first transmission signal by 180 degrees. That is, the second transmission signal is a phase-inverted version of the signal waveform of the first transmission signal.

The second transmission signal which is generated as described above is expressed by the periodic function −f(t). Here, similarly to the first transmission signal, the first fundamental component and the second fundamental component become dominant in the component of the waveform of the second transmission signal which passes through the ultrasound probe 2. Therefore, the periodical function −f(t) can be approximately expressed by the following formula (10).

[Numerical formula 6]

$$-f(t) \cong -b_1\sin\left(\frac{2\pi}{T_0}t\right) + a_2\cos\left(\frac{4\pi}{T_0}t\right) \quad (10)$$

$$= -\frac{4}{\pi}\cos\left(2\pi\frac{A}{T_0}\right)\cdot\sin\left(\frac{2\pi}{T_0}t\right) - \frac{2}{\pi}\sin\left(4\pi\frac{A}{T_0}\right)\cdot\cos\left(\frac{4\pi}{T_0}t\right)$$

Therefore, the transmission ultrasound wave where the first fundamental component and the second fundamental component expressed by the above formula (10) are the main components is output by the ultrasound probe 2.

Figure 7:
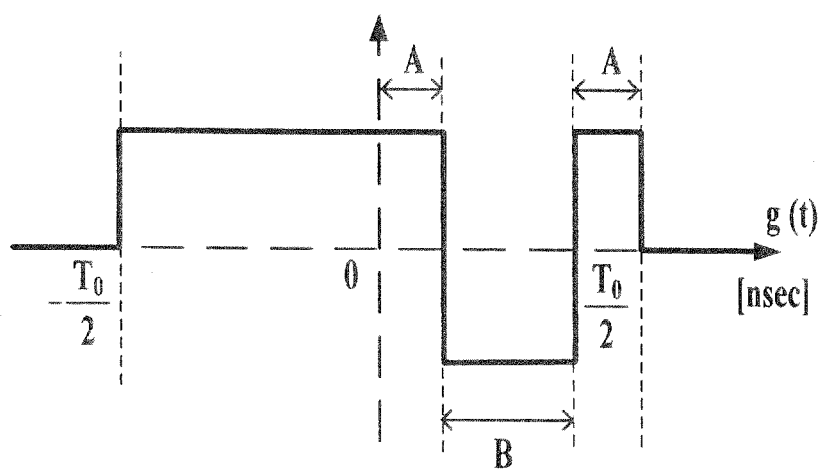
FIG. 7 is a diagram for explaining a waveform of the third transmission signal.

Next, the transmitting unit 12 generates the third transmission signal by the driving signal waveform setting unit 123. As shown in FIG. 7, the third transmission signal is the time-inverted version of the signal waveform of the first transmission signal and for example, the third transmission signal is formed by performing time inversion (inversion of the direction of time axis) on the signals waveform of the first transmission signal formed of the pulse from $-T_0/2$ to $T_0/2$. Here, the third transmission signal may be formed first and then, the first transmission signal may be formed by performing time inversion on the third transmission signal.

As shown in FIG. 7, the third transmission signal which is generated as described above is expressed by the periodical function g(t). Here, similarly to the first transmission signal, the first fundamental component and the second fundamental component are dominant in the component of the waveform of the third transmission signal which passes through the ultrasound probe 2. Therefore, the periodical function g(t) can be approximately expressed by the following formula (11).

[Numerical formula 7]

$$\begin{aligned} g(t) &= f(-t) \\ &\cong b_1 \sin\left\{\frac{2\pi}{T_0}(-t)\right\} + a_2 \cos\left\{\frac{4\pi}{T_0}(-t)\right\} \\ &= \frac{4}{\pi}\cos\left(2\pi\frac{A}{T_0}\right)\cdot\sin\left\{\frac{2\pi}{T_0}(-t)\right\} + \frac{2}{\pi}\sin\left(4\pi\frac{A}{T_0}\right)\cdot\cos\left\{\frac{4\pi}{T_0}(-t)\right\} \\ &= -\frac{4}{\pi}\cos\left(2\pi\frac{A}{T_0}\right)\cdot\sin\left(\frac{2\pi}{T_0}t\right) + \frac{2}{\pi}\sin\left(4\pi\frac{A}{T_0}\right)\cdot\cos\left(\frac{4\pi}{T_0}t\right) \end{aligned} \quad (11)$$

Therefore, the transmission ultrasound wave wherein the first fundamental component and the second fundamental component expressed by the above formula (11) are the main components is output from the ultrasound probe 2.

Next, the transmitting unit 12 generates the fourth transmission signal by the driving signal waveform setting unit 123. The fourth transmission signal is a phase-inverted and time-inverted version of the signal waveform of the first transmission signal and for example, the fourth transmission signal is formed by performing phase inversion and time inversion on the signal waveform of the first transmission signal.

The fourth transmission signal generated as described above is expressed by the periodical function −g(t). Here, similarly to the first transmission signal, the first fundamental component and the second fundamental component are dominant in the component of the waveform of the fourth transmission signal which passes through the ultrasound probe 2. Therefore, the periodical function −g(t) can be approximately expressed by the following formula (12).

[Numerical formula 8]

$$\begin{aligned} -g(t) &\cong b_1 \sin\left(\frac{2\pi}{T_0}t\right) - a_2 \cos\left(\frac{4\pi}{T_0}t\right) \\ &= \frac{4}{\pi}\cos\left(2\pi\frac{A}{T_0}\right)\cdot\sin\left(\frac{2\pi}{T_0}t\right) + \frac{2}{\pi}\sin\left(4\pi\frac{A}{T_0}\right)\cdot\cos\left(\frac{4\pi}{T_0}t\right) \end{aligned} \quad (12)$$

Therefore, the transmission ultrasound wave wherein the first fundamental component and the second fundamental component expressed by the above formula (12) are the main components is output by the ultrasound probe 2.

Figure 8:
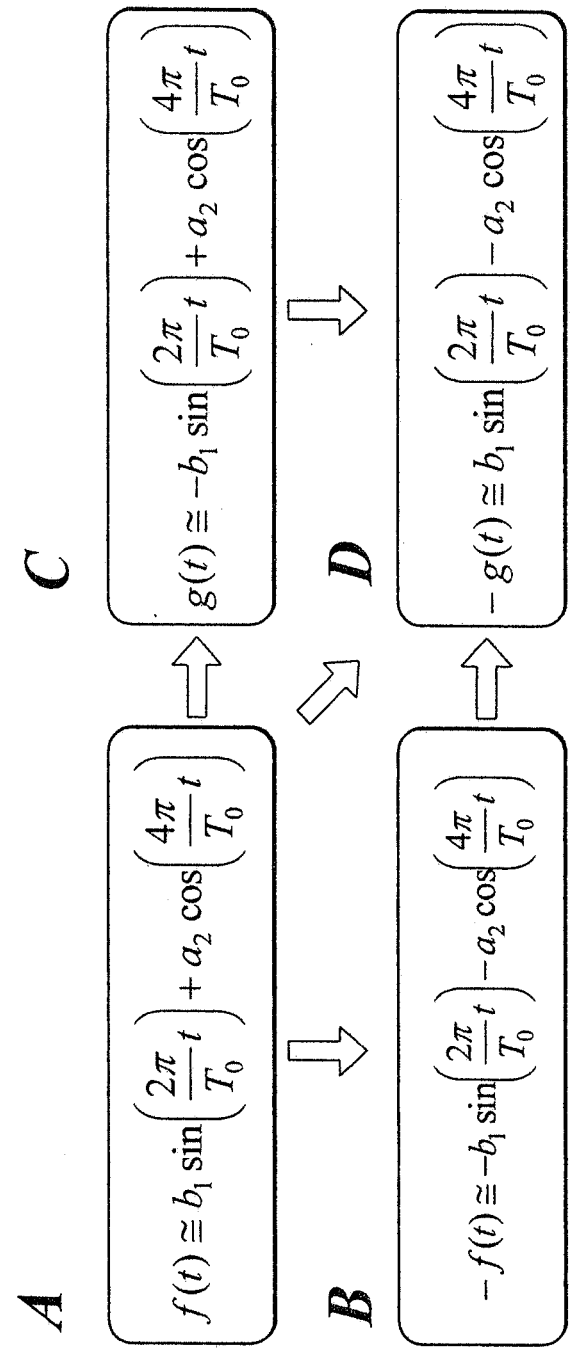
FIG. 8 is a diagram for explaining a relation between the first to the fourth transmission signals.

The first to the fourth transmission signals which are generated as described above can be expressed having a relation as shown in FIGS. 8A to 8D. Here, with respect to the signal waveform of the first transmission signal expressed by the periodical function f(t) shown in FIG. 8A, it can be understood that sine wave appears when n=1 and cosine wave appears when n=2 by the Fourier series expansion. Further, when the signal waveform of the first transmission signal expressed by the periodic function f(t) shown in FIG. 8A is phase inverted, the second transmission signal expressed by the periodic function −f(t) where the signs of the first member and the second member of the formula of the periodic function −f(t) are inversed is generated as shown in FIG. 8B. This means the same as displacing the phases of sine wave and cosine wave by 180 degrees in the signal waveform of the first transmission signal expressed by the periodical function f(t). Further, when the signal waveform of the first transmission signal expressed by the periodical function f(t) is time inverted, the third transmission signal expressed by the periodic function g(t) where the sign of the first member of the formula of the periodic function g(t) is inversed is generated as shown in FIG. 8C. This means the same as displacing only the phase of sine wave by 180 degrees in the signal waveform of the first transmission signal expressed by the periodical function f(t). Further, when the signal waveform of the first transmission signal expressed by the periodical function f(t) is phase inverted and time inverted, the fourth transmission signal expressed by the periodical function −g(t) where the sign of the second member of the formula of the periodical function −g(t) is inversed is generated as shown in FIG. 8D. This means the same as displacing only the phase of cosine wave by 180 degrees in the signal waveform of the first transmission signal expressed by the periodical function f(t). Here, the fourth transmission signal can be obtained when the signal waveform of the second transmission signal shown in FIG. 8B is time inverted. Further, the fourth transmission signal can be obtained also when the signal waveform of the third transmission signal shown in FIG. 8C is phase inverted.

Figure 9A:
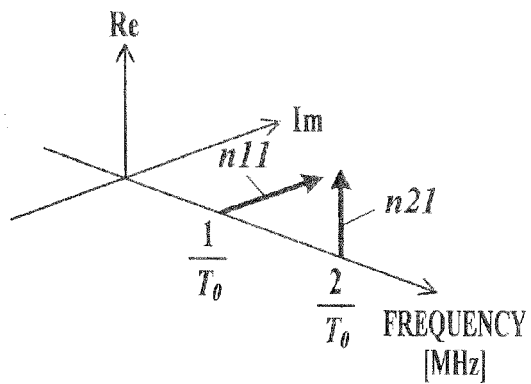
FIG. 9A is a diagram expressing a signal waveform of the first transmission signal.
Figure 9C:
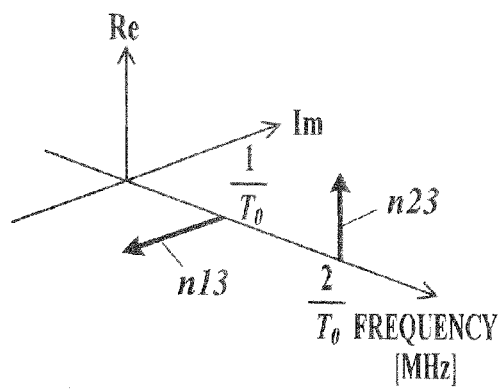
FIG. 9C is a diagram expressing a signal waveform of the third transmission signal.
Figure 9B:
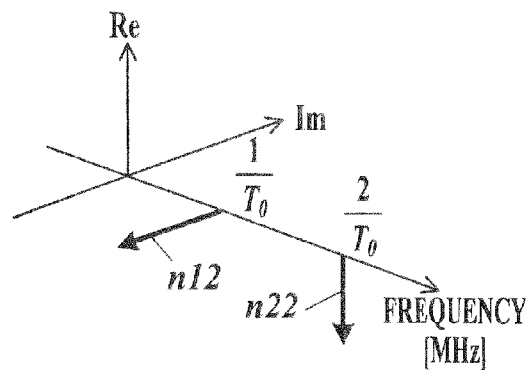
FIG. 9B is a diagram expressing a signal waveform of the second transmission signal.
Figure 9D:
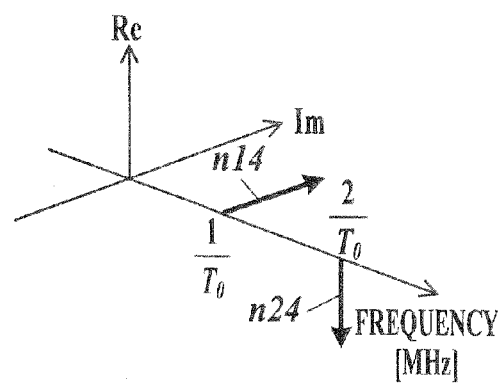
FIG. 9D is a diagram expressing a signal waveform of the fourth transmission signal.

FIGS. 9A to 9D express the relation between the signal waveforms of the first to the fourth transmission signals shown in FIGS. 8A to 8D in terms of frequency space. In FIGS. 9A to 9D, "Im" indicates an axis of imaginary number and "Re" indicates an axis of real number. FIG. 9A shows the phase of sine wave (the first fundamental component n11) and the phase of cosine wave (the second fundamental component n21) included in the signal waveform of the first transmission signal. FIG. 9B shows the phase of sine wave (the first fundamental component n12) and the phase of cosine wave (the second fundamental component n22) included in the signal waveform of the second transmission signal. FIG. 9C shows the phase of sine wave (the first fundamental component n13) and the phase of cosine wave (the second fundamental component n23) included in the signal waveform of the third transmission signal. FIG. 9D shows the phase of sine wave (the first fundamental component n14) and the phase of cosine wave (the second fundamental component n24) included in the signal waveform of the fourth transmission signal.

As shown in FIGS. 9A to 9D, it can be understood that the first fundamental component n11 and the second fundamental component n21 included in the first transmission signal and the first fundamental component n12 and the second fundamental component n22 included in the second transmission signal are antiphase of each other, respectively. Further, it can be understood that the first fundamental component n13 and the second fundamental component n23 included in the third transmission signal and the first fundamental component n14 and the second fundamental component n24 included in the fourth transmission signal are antiphase of each other, respectively.

Figure 10:
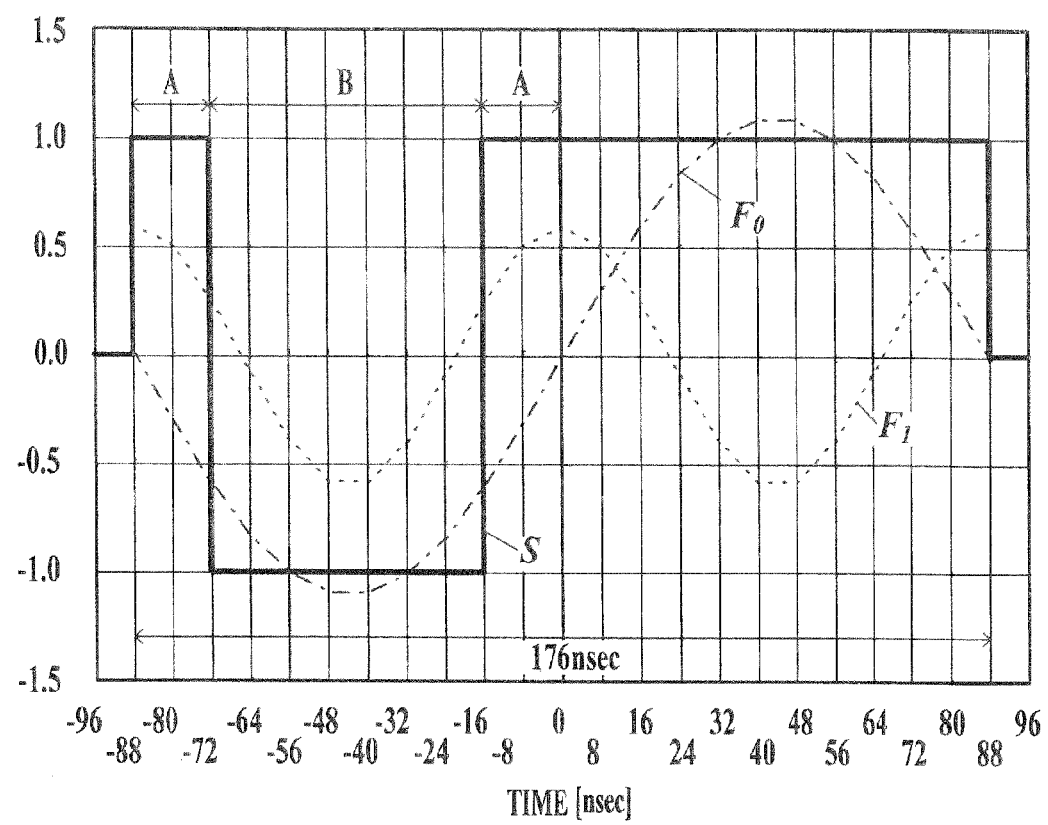
FIG. 10 is a diagram for explaining an example of waveform of the first transmission signal.

In the embodiment, the transmitting unit 12 generates the first transmission signal S of square wave as shown in FIG. 10 as an example of signal waveform most appropriate for forming the first transmission signal. In this first transmission signal S, one cycle is 176 nsec, the parameter A is set to 16 nsec and the parameter B is set to 56 nsec. That is, after intensity of the first transmission signal S rises to 1.0 from 0 at the initial part of a cycle, the intensity of the first transmission signal S falls to −1.0 from 1.0 at the time when 16 nsec defined by the parameter A elapses. Thereafter, the intensity of the first transmission signal S rises to 1.0 from −1.0 at the time when 56 nsec defined by the parameter B elapses, and further, the signal waveform for a half cycle (88 nsec) is formed so that the intensity of the first transmission signal S maintains the state of 1.0 during 16 nsec defined by the parameter A. Then, the signal waveform is formed to that the intensity of the first transmission signal S is maintained at 1.0 until the final part of the cycle and then falls to 0.

When the Fourier series expansion is performed on the first transmission signal S formed as described above, it can be understood that the first fundamental component $F_0$ of 5.7 MHz and the second fundamental component $F_1$ of 11.4 MHz which is double the frequency of the first fundamental component $F_0$ are included.

Figure 11:
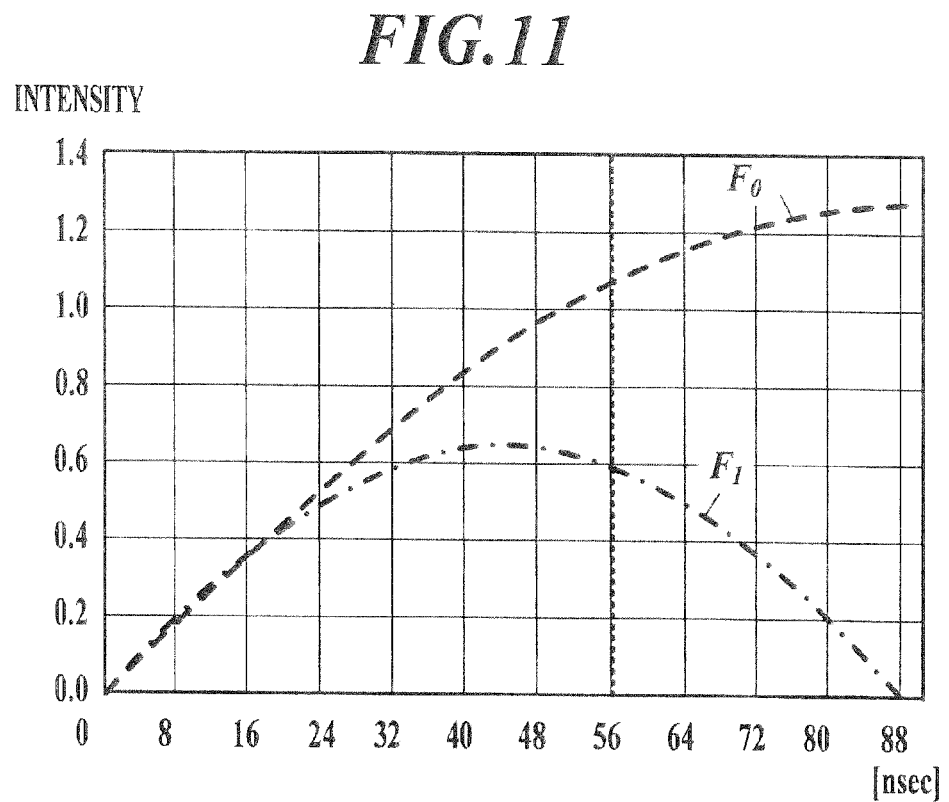
FIG. 11 is a diagram showing a relation between elapsed time and intensity of fundamental components.

In the embodiment, the parameter B of the first transmission signal S is set according to the following logic. FIG. 11 shows a relation between elapsed time since square wave signals of the first fundamental component $F_0$ and the second fundamental component $F_1$ and intensity of each of the fundamental components, and FIG. 12 shows intensity product $F_p$ obtained by multiplying the intensity of the first fundamental component $F_0$ and the intensity of the second fundamental component $F_1$.

Figure 12:
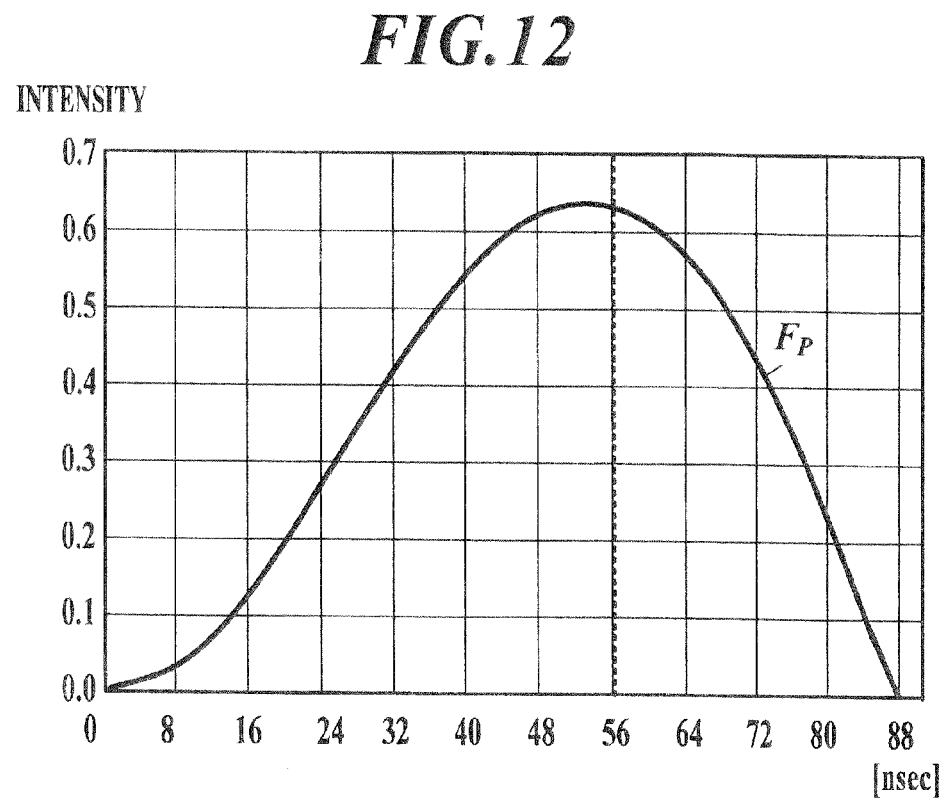
FIG. 12 is a diagram showing intensity product of the first fundamental component and the second fundamental component.

As shown in FIG. 12, the intensity product $F_p$ of the first fundamental component $F_0$ and the second fundamental component $F_1$ indicates the greatest value at the time when about 53 nsec elapses after the signal of square wave rises. Setting the parameter B to the time that indicates the greatest value is optimum because the difference frequency component is generated most effectively and also loss in the first fundamental component $F_0$ is about 84% of the greatest value indicated at the time when 88 nsec elapses after the signal of square wave rises. In the embodiment, the parameter A and the parameter B are set in increments of 8 nsec, for example. Therefore, the parameter B is set to 56 nsec approximate to the above described 53 nsec.

Here, the parameter A and the parameter B are not limited to what are set as described above and can be set arbitrarily according to various types of conditions. However, it is preferred that the parameter A and the parameter B are not equal to each other.

Next, a nonlinear component which is generated by the ultrasound wave output due to the first to the fourth transmission signals which are generated as described above being input to the ultrasound probe 2 transmitting inside a subject will be described.

It is known that transmission of ultrasound wave indicates the behavior expressed by a nonlinear wave equation when the sound pressure thereof is significantly high. The nonlinear wave equation expresses the behavior of the original ultrasound wave which is transmitted while generating various types of frequency components due to interference of the frequency components included in the original waveform of the ultrasound wave, and the frequency components generated due to such transmission of ultrasound wave is called harmonic components (nonlinear components). Because such harmonic components can be close simply by being time derivative of square of the waveform of the transmitted ultrasound wave, harmonic components to be generated can be estimated if the waveform (fundamental) of the ultrasound wave which is the original of transmission can be specified.

According to the above logic, harmonic components which is generated due to the ultrasound wave output by the first transmission signal expressed by the periodical function f(t) shown in the above formula (9) being applied to the ultrasound probe 2 can be expressed by the following formula (13).

[Numerical formula 9]

$$\frac{\partial f(t)^2}{\partial t} \cong b_1^2\left(2 \cdot \frac{2\pi}{T_0}\right)\sin\left(2 \cdot \frac{2\pi}{T_0}t\right) + a_2 b_1\left(\frac{2\pi + 4\pi}{T_0}\right)\cos\left(\frac{2\pi + 4\pi}{T_0}t\right) + \quad (13)$$
$$a_2 b_1\left(\frac{2\pi - 4\pi}{T_0}\right)\cos\left(\frac{2\pi - 4\pi}{T_0}t\right) + a_2^2\left(2 \cdot \frac{4\pi}{T_0}\right)\sin\left(2 \cdot \frac{4\pi}{T_0}t\right)$$

Here, band of the ultrasound wave that passes through is defined by the band characteristic of the ultrasound probe 2. As a result, among the harmonic component shown in the above formula (13), the second harmonic component as a higher harmonic component which is double the frequency component of the first fundamental component indicated in the first member of the above formula (13) and the difference frequency component which is generated as a result of the nonlinear effect of the first fundamental component and the second fundamental component indicated in the third member of the above formula (13) pass through the ultrasound probe 2. That is, the harmonic component which passes through the ultrasound probe 2 can be expressed by the following formula (14).

[Numerical formula 10]

$$\frac{\partial f(t)^2}{\partial t} \cong b_1^2\left(\frac{4\pi}{T_0}\right)\sin\left(\frac{4\pi}{T_0}t\right) - a_2 b_1\left(\frac{2\pi}{T_0}\right)\cos\left(\frac{2\pi}{T_0}t\right) \quad (14)$$

Figure 13A:
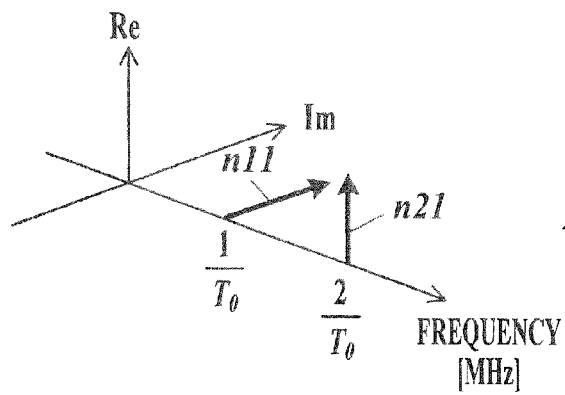
FIG. 13A is a diagram for explaining a relation between phases of harmonic components of reflection ultrasound wave with respect to a transmission signal.
Figure 13B:
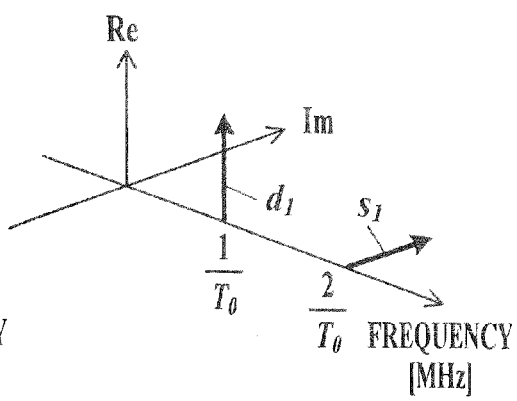
FIG. 13B is a diagram for explaining a relation between phases of harmonic components of reflection ultrasound wave with respect to a transmission signal.

FIGS. 13A and 13B show the harmonic component included in the reflection ultrasound obtained from the ultrasound wave output due to the first transmission signal shown in the above formula (14) is to be expressed in terms of frequency space. Here, FIG. 13A expresses the first fundamental component n11 and the second fundamental component n21 included in the signal waveform of the first transmission signal and FIG. 13B shows the second harmonic component $s_1$ of the first fundamental component n11 and the difference frequency component $d_1$ of the first fundamental component n11 and the second fundamental component n21. As shown in FIG. 13B, it can be understood that the phases of the second harmonic component $s_1$ and the difference frequency component $d_1$ are different.

Moreover, with respect to the harmonic component generated due to the ultrasound wave which is output by the second transmission signal indicated by the periodical function −f(t) shown in the above formula (10) being applied to the ultrasound probe 2, this can be expressed similarly as the first transmission signal by the above formula (13).

Further, with respect to the harmonic component generated due to the ultrasound wave which is output by the third transmission signal indicated by the periodical function g(t) shown in the above formula (11) being applied to the ultrasound probe 2, this can be expressed by the following formula (15).

[Numerical formula 11]

$$\frac{\partial g(t)^2}{\partial t} \cong b_1^2 \left(\frac{4\pi}{T_0}\right) \sin\left(\frac{4\pi}{T_0}t\right) + a_2 b_1 \left(\frac{2\pi}{T_0}\right) \cos\left(\frac{2\pi}{T_0}t\right) \quad (15)$$

Similarly, with respect to the harmonic component generated due to the ultrasound wave which is output by the fourth transmission signal indicated by the periodical function −g(t) shown in the above formula (12) being applied to the ultrasound probe 2, this can be expressed by the above formula (15).

Figure 14A:
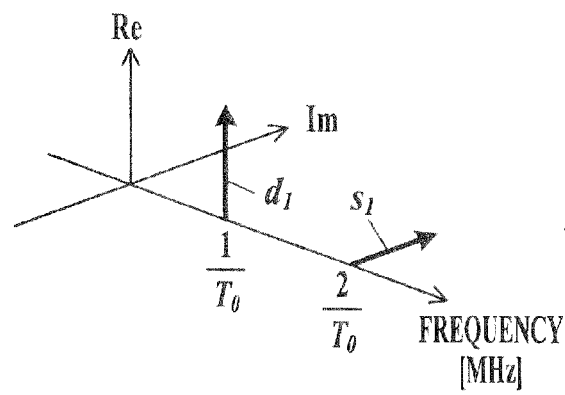
FIG. 14A is a diagram for explaining a relation between phases of harmonic components of reflection ultrasound wave with respect to a transmission signal.
Figure 14B:
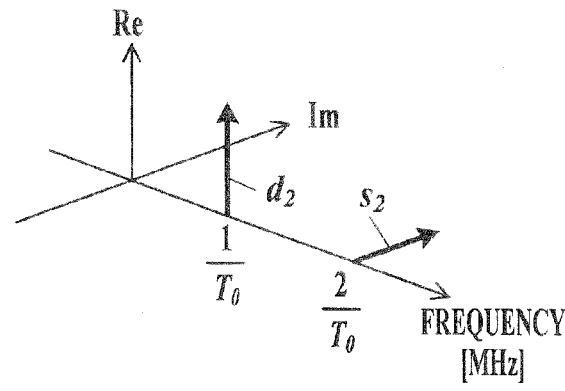
FIG. 14B is a diagram for explaining a relation between phases of harmonic components of reflection ultrasound wave with respect to a transmission signal.
Figure 14C:
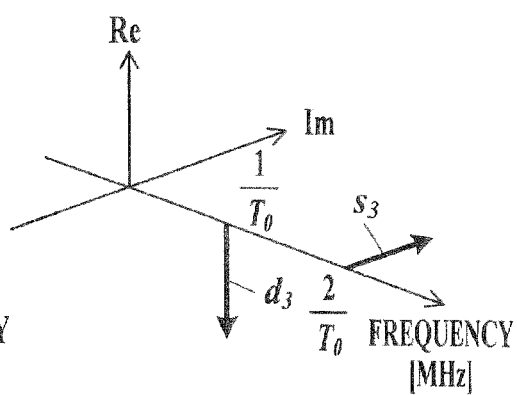
FIG. 14C is a diagram for explaining a relation between phases of harmonic components of reflection ultrasound wave with respect to a transmission signal.
Figure 14D:
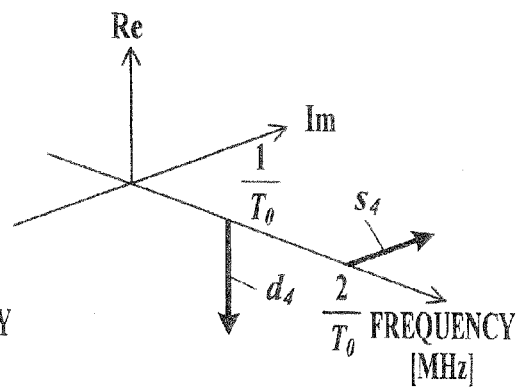
FIG. 14D is a diagram for explaining a relation between phases of harmonic components of reflection ultrasound wave with respect to a transmission signal.

FIGS. 14A to 14D show the relation between the harmonic components included in the reflection ultrasound waves obtained from the ultrasound waves output by the above mentioned first to fourth transmission signal in terms of frequency space. FIG. 14A shows the phase of the second harmonic component $s_1$ and the phase of the difference frequency component $d_1$ included in the reflection ultrasound wave obtained from the ultrasound wave output due to the first transmission signal. FIG. 14B shows the phase of the second harmonic component $s_2$ and the phase of the difference frequency component $d_2$ included in the reflection ultrasound wave obtained from the ultrasound wave output due to the second transmission signal. FIG. 14C shows the phase of the second harmonic component $s_3$ and the phase of the difference frequency component $d_3$ included in the reflection ultrasound wave obtained from the ultrasound wave output due to the third transmission signal. FIG. 14D shows the phase of the second harmonic component $s_4$ and the phase of the difference frequency component $d_4$ included in the reflection ultrasound wave obtained from the ultrasound wave output due to the fourth transmission signal.

As shown in FIGS. 14A to 14D, it can be understood that the second harmonic component $s_1$ and the difference frequency component $d_1$ included in the reflection ultrasound wave corresponding to the first transmission signal and the second harmonic component $s_2$ and the difference frequency component $d_2$ included in the reflection ultrasound wave corresponding to the second transmission signal are in-phase, respectively. Further, the second harmonic component $s_3$ and the difference frequency component $d_3$ included in the reflection ultrasound wave corresponding to the third transmission signal and the second harmonic component $s_4$ and the difference frequency component $d_4$ included in the reflection ultrasound wave corresponding to the fourth transmission signal are in-phase, respectively.

Moreover, as shown in FIGS. 14A to 14D, it can be understood that the second harmonic component $s_1$ included in the reflection ultrasound wave corresponding to the first transmission signal, the second harmonic component $s_2$ included in the reflection ultrasound wave corresponding to the second transmission signal, the second harmonic component $s_3$ included in the reflection ultrasound wave corresponding to the third transmission signal and the second harmonic component $s_4$ included in the reflection ultrasound wave corresponding to the fourth transmission signal are all in-phase. This is because the second harmonic components are obtained by square of the first fundamental component.

Difference components are generated as a result of nonlinear effect of the first fundamental components and the second fundamental components.

The first transmission signal and the second transmission signal are in phase inversion relation with each other and the phase relations between the first fundamental component and the second fundamental component thereof are practically the same. Therefore, the difference frequency component $d_1$ included in the reflection ultrasound wave corresponding to the first transmission signal and the difference component $d_2$ included in the reflection ultrasound wave corresponding to the second transmission signal are in-phase as shown in FIGS. 14A to 14D.

Moreover, because the third transmission signal and the fourth transmission signal are in a time inversion relation with the first transmission signal, the phase relations between the first fundamental component and the second fundamental component thereof are different from that in the first transmission signal. Therefore, the phase of the difference frequency component $d_3$ included in the reflection ultrasound wave corresponding to the third transmission signal and the phase to the difference frequency component $d_4$ included in the reflection ultrasound wave corresponding to the fourth transmission signal appear as antiphase of the difference frequency component $d_1$ included in the reflection ultrasound wave corresponding to the first transmission signal as shown in FIGS. 14A to 14D.

Generation method of ultrasound image data on the basis of received signals obtained by receiving reflection ultrasound waves corresponding to transmission ultrasound waves transmitted from the ultrasound probe 2 due to the first to the fourth transmission signals as described above will be described.

First, with respect to each of received signals obtained by reflection ultrasound waves corresponding to transmission ultrasound waves transmitted due to the first to the fourth transmission signals as described above being converted into electric signals by the ultrasound probe 2, the receiving unit 13 of the ultrasound diagnostic imaging apparatus S generates sound ray data (the first to the fourth sound ray data) by performing the above described processing by the AMP 131, the ADC 132 and the phasing addition unit 133 and stores the sound ray data in the sound ray memory 134, each in difference region. Here, the received signal obtained from the reflection ultrasound wave corresponding to the transmission ultrasound wave transmitted due to the first transmission signal is called the first received signal, the received signal obtained from the reflection ultrasound wave corresponding to the transmission ultrasound wave transmitted due to the second transmission signal is called the second received signal, the received signal obtained from the reflection ultrasound wave corresponding to the transmission ultrasound wave transmitted due to the third transmission signal is called the third received signal and the received signal obtained from the reflection ultrasound wave corresponding to the transmission ultrasound wave transmitted due to the fourth transmission signal is called the fourth received signal.

When each of the first to the fourth sound ray data is stored in the sound ray memory 134 as described above, the signal component extraction unit 135 extracts a harmonic component as described below and further separates a second harmonic component and a difference frequency component from the extracted harmonic component.

Here, in ultrasound image, it is known that a high resolution image with low-artifact can be obtained by imaging only the harmonic component included in the received signals. Therefore, various techniques for taking out only the harmonic component from the received signals and imaging the harmonic component are known. Pulse inversion is one of the well known techniques for taking out only the harmonic component from the received signals. This is a technique utilizing the phase invariant characteristic of harmonic component, and in the technique, by two transmission ultrasound waves having inversed phases being transmitted and by the received signals obtained from the reflection ultrasound waves corresponding to the two transmission ultrasound waves being added, fundamental components included in the received signals are removed and only the harmonic components are extracted.

In the embodiment, this technique of pulse inversion is used to extract the harmonic components and then, second harmonic components and difference frequency components are separated from the harmonic components.

Figure 15:
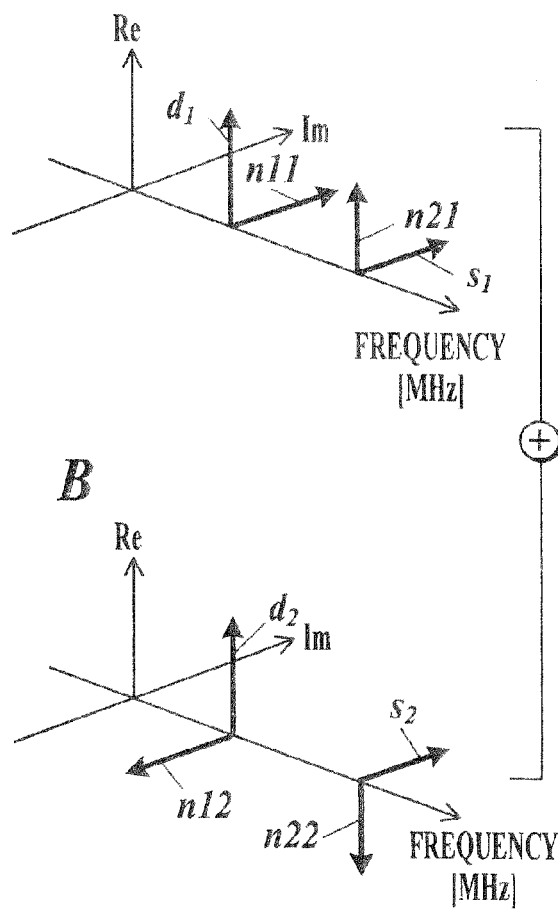
FIG. 15 is a diagram for explaining a procedure for extracting harmonic components.

The signal component extraction unit 135 reads out the first sound ray data and the second sound ray data from the sound ray memory 134 and generates the first compound data by adding the first and the second sound ray data. That is, by adding the first sound ray data and the second sound ray data, the signal component extraction unit 135 generates the first compound data wherein fundamental components are removed and the harmonic components are emphasized. That is, when the first sound ray data and the second sound ray data are added, because the first fundamental component n11 and the second fundamental component n21 included in the first sound ray data shown in FIG. 15A are antiphase of the first fundamental component n21 and the second fundamental component n22 included in the second sound ray data shown in FIG. 15B, respectively, the first fundamental components and the second fundamental components cancel each other out, respectively and they are removed as shown in FIG. 15C. On the other hand, the second harmonic component $s_1$ and the difference frequency component $d_1$ included in the first sound ray data shown in FIG. 15A are in-phase with the second harmonic component $s_2$ and the difference frequency component $d_2$ included in the second sound ray data shown in FIG. 15B, respectively. Therefore, the second harmonic component $s_{12}$ and the difference frequency component $d_{12}$ are emphasized in the sound ray data after the addition, that is, in the first component data as shown in FIG. 15C. In such way, the signal component extraction unit 135 carries out extraction of harmonic components from the first received signal (the first sound ray data) and the second received signal (the second sound ray data).

Further, the signal component extraction unit 135 similarly reads out the third sound ray data and the fourth sound ray data from the sound ray memory 134 and generates the second compound data by adding the third sound ray data and the fourth sound ray data. As a result, the first fundamental components and the second fundamental components cancel each other out and the second component data wherein the second harmonic component $s_{34}$ and the difference frequency component $d_{34}$ (see FIG. 16B) are emphasized is generated. In such way, the signal component extraction unit 135 carries out extraction of harmonic components from the third received signal (the third sound ray data) and the fourth received signal (the fourth sound ray data).

Figure 16:
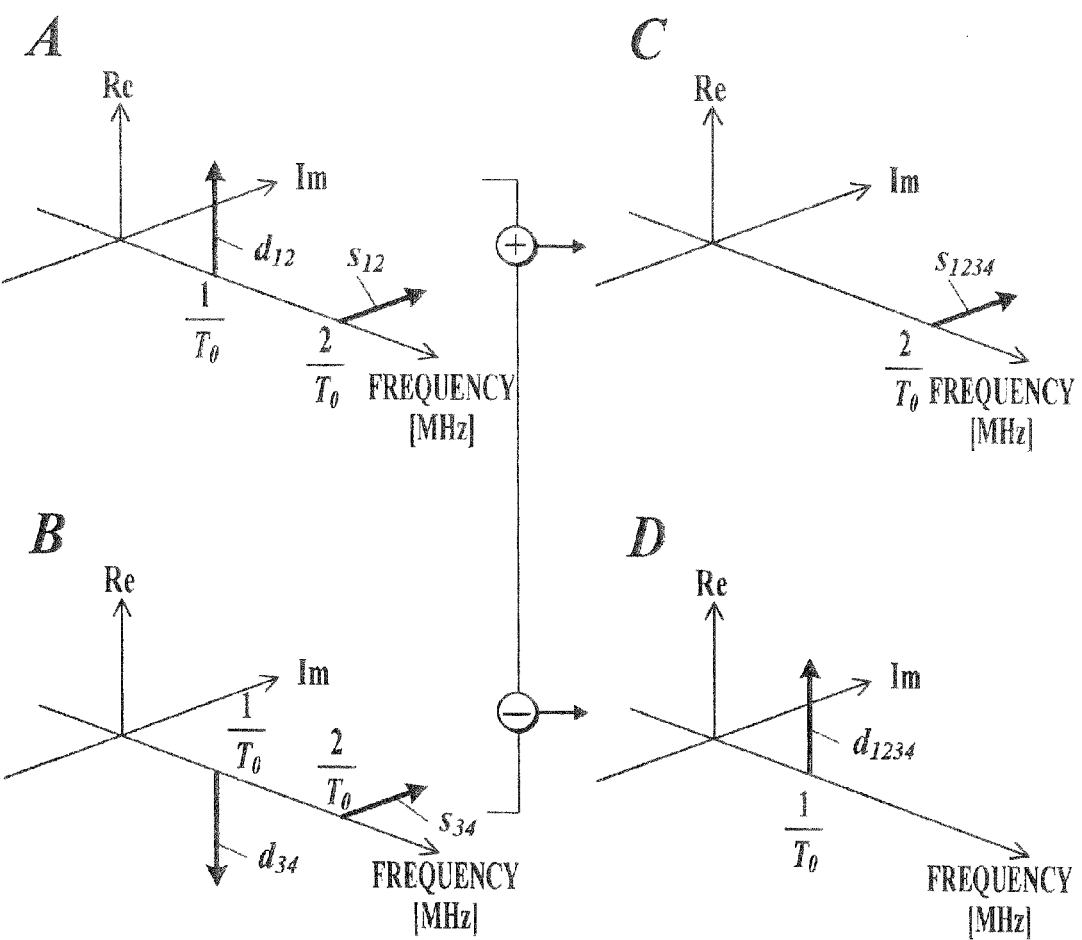
FIG. 16 is a diagram for explaining a procedure for separating and extracting a second harmonic component and a difference frequency component.

Further, the signal component extraction unit 135 separates the second harmonic components and the difference frequency components as described below from the first compound data and the second compound data obtained as described above. That is, with respect to the first compound data shown in FIG. 16A and the second compound data shown in FIG. 16B, their second harmonic components are in-phase and their difference frequency components are antiphase of each other. Therefore, first, the signal component extraction unit 135 can generate the third compound data wherein the difference frequency components are removed and the second harmonic component $s_{1234}$ is emphasized as shown in FIG. 16C by adding the first compound data and the second compound data. Further, the signal component extraction unit 135 can generate the fourth compound data wherein the second harmonic components are removed and the difference frequency component $d_{1234}$ is emphasized as shown in FIG. 16D due to subtraction of the first compound data and the second compound data.

Incidentally, according to the conventional technique of pulse inversion, although harmonic component can be extracted from the received signals, second harmonic components and difference frequency components cannot be separated and extracted because second harmonic components and difference frequency components are mixed in complete harmony in the extracted harmonic component. In the embodiment, by having the configuration as described above, second harmonic components and difference frequency components can be separated and extracted from the harmonic component.

The signal component extraction unit 135 outputs the third compound data generated as described above to the band adjustment filter 136a and outputs the fourth compound data to the band adjustment filter 136b. The compound data to which filter processing is performed by the band adjustment filters 136a and 136b are input in the phase adjustment filters 137a, 137b, respectively.

Here, phase adjusting method of harmonic component used in the embodiment will be described.

Figure 17A:
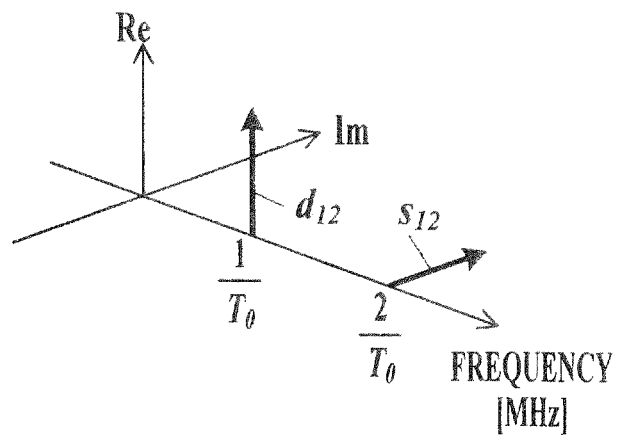
FIG. 17A is a diagram for explaining bands of a second harmonic component and a difference frequency component.

FIG. 17A shows the first component data. That is, the sound ray data shown in terms of frequency space in FIG. 17A is sound ray data in which the harmonic component is emphasized due to the conventional pulse inversion by adding the first sound ray data and the second sound ray data.

Figure 17B:
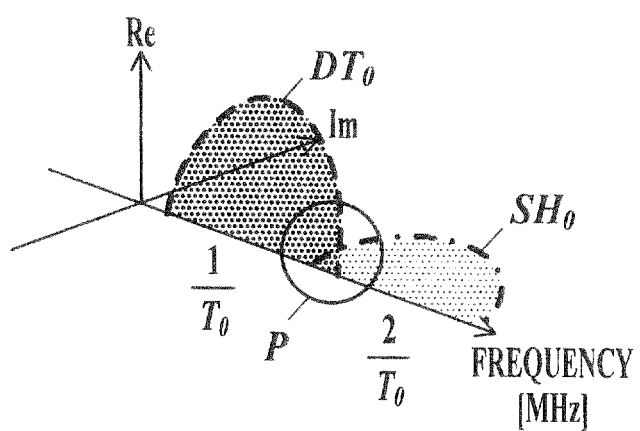
FIG. 17B is a diagram for explaining bands of a second harmonic component and a difference frequency component.

The second harmonic component $s_{12}$ and the difference frequency component $d_{12}$ are included in the first compound data shown in FIG. 17A. In practice, because these harmonic components are formed of a waveform of finite length, they each have a band of a certain broadness as shown in FIG. 17B. There are cases where these bands of harmonic components overlap each other in a certain frequency band. In the example shown in FIG. 17B, the low frequency area in the band $SH_0$ of the second harmonic component overlap with the high frequency area in the band $DT_0$ of the difference frequency component. In the region P where the band $SH_0$ of the second harmonic component and the band $DT_0$ of the difference frequency component overlap each other in such way, phase interference of the two harmonic components occurs and intensity of the signals reinforce each other or weaken each other depending on the phase state of the harmonic components.

Figure 18:
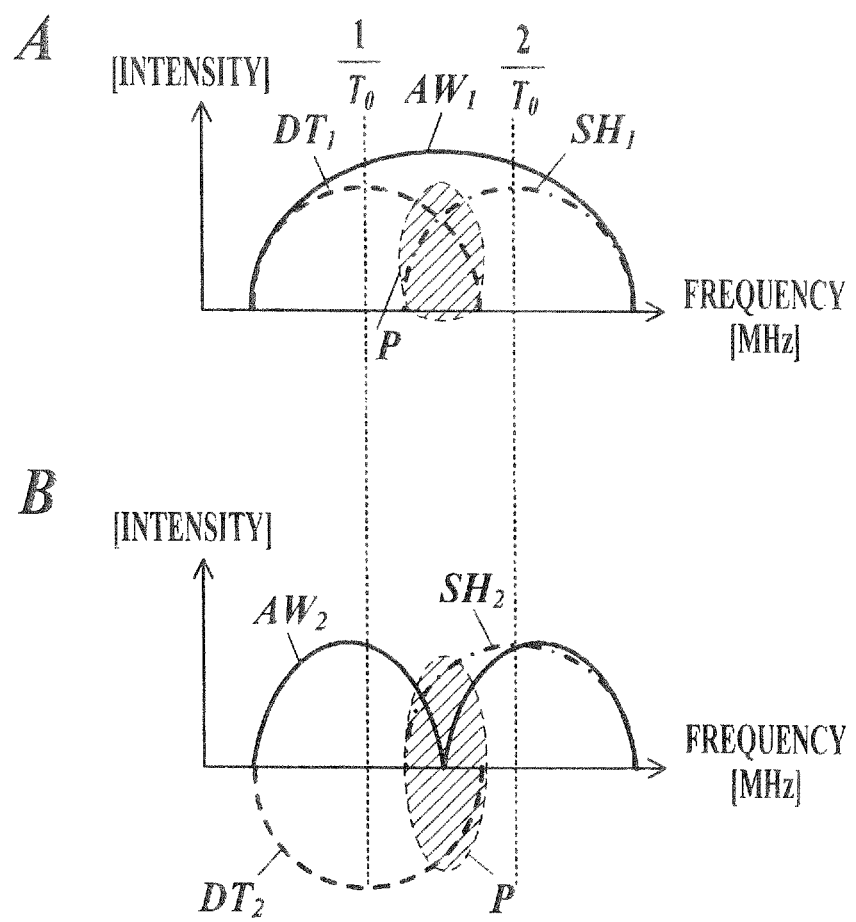
FIG. 18 is a diagram for explaining a band of harmonic components.

In particular, for example, when the phase of the band $SH_1$ of the second harmonic component and the phase of the band $DT_1$ of the difference frequency component approximate each other as shown in FIG. 18A, they are in a relation where intensity of signals reinforce each other and as a result of the second harmonic component and the difference frequency component overlapping each other, there appears the band $AW_1$ of harmonic component where the band is enlarged. When sound ray data including such band $AW_1$ of harmonic component can be obtained, time resolution is improved and therefore, an ultrasound image of high resolution and high quality can be obtained.

On the other hand, for example, when the phase of the band $SH_2$ of the second harmonic component and the phase of the band $DT_2$ of the difference frequency component are apart from each other as shown in FIG. 18B, the phases are to be in a relation where they weaken each other's signal intensity and as a result of the second harmonic component and the difference frequency component overlapping, a band $AW_2$ of harmonic component where its band is narrow appears. Such band $AW_2$ of harmonic component has a cleavage in the band and the band is separated. Therefore, even when harmonic component is extracted, high quality ultrasound image cannot be expected.

In the conventional ultrasound diagnostic imaging apparatus, second harmonic component and difference frequency component cannot be separated and extracted by performing signal processing on received signals. Therefore, for example, signal waveform of a transmission signal is adjusted so that the phase of second harmonic component and the phase of difference frequency component approximate each other. However, controlling so that the phases of such harmonic components always be in a good condition is difficult because of unevenness in the subject medium through which ultrasound wave transmits, bad accuracy in beam forming that occurs due to the unevenness and the like. Therefore, even when transmission ultrasound wave is transmitted after adjusting the signal waveform of a transmission signal and harmonic components are extracted from received signals obtained from the reflection ultrasound waves, there are cases where the received signal which causes the second harmonic component and the difference frequency component weaken each other is obtained as shown in FIG. 18B.

Further, second harmonic component and difference frequency component were tried to be separated by using a band limiting filter. However, in a received signal where second harmonic component and difference frequency component are mixed in a complete harmony, high quality ultrasound image cannot be expected because phase state cannot be separated.

In view of the above, in the embodiment, because second harmonic component and difference frequency component can be separated and extracted from received signals as described above, the phase of second harmonic component and the phase of difference frequency component can be adjusted freely by the phase adjustment filters 137a and 137b, respectively. That is, the phase of second harmonic component and the phase of difference frequency component can be approximate to each other relatively and the band of harmonic components can be broad.

For example, when the phase of the band $SH_2$ of the second harmonic component and the phase of the band $DT_2$ of the difference frequency component are separated from each other by 180 degrees as shown in FIG. 19A, as shown in FIG. 19B and FIG. 19C, the phase of the difference frequency component need to be shifted for 180 degrees by the phase adjustment filter 137b after separating the second harmonic component and the difference frequency component by the signal component extraction unit 135. Then, the band $DT_2$ of the difference frequency component of which the phase is changed approximates the band $SH_2$ of the second harmonic component as shown in FIG. 19D. Further, by adding the harmonic components by the signal adder 138, sound ray data having the band $AW_{2a}$ of harmonic component of broadband where the band is broaden can be obtained.

(Second Embodiment)

Next, the second embodiment will be described. In the second embodiment, after separating and extracting second harmonic component and difference frequency component as described above, brightness conversion is performed on each harmonic component instead of adjusting each phase and then, ultrasound image data is obtained by adding the harmonic components in which brightness is converted (compound processing). By adding brightness data obtained by performing brightness conversion on the second harmonic component and brightness data obtained by performing brightness conversion on the difference frequency component, speckle and noise (hereinafter, called noise and the like) are suppressed and spatial resolution of an ultrasound image can be improved.

The second embodiment is different from the first embodiment in the aspect that the receiving unit 13 and the image generation unit 14 of the ultrasound diagnostic imaging apparatus S are changed. Here, with respect to functional configurations similar to those in the ultrasound diagnostic imaging apparatus S of the first embodiment, the same reference numerals are used and their descriptions are omitted.

Figure 20:
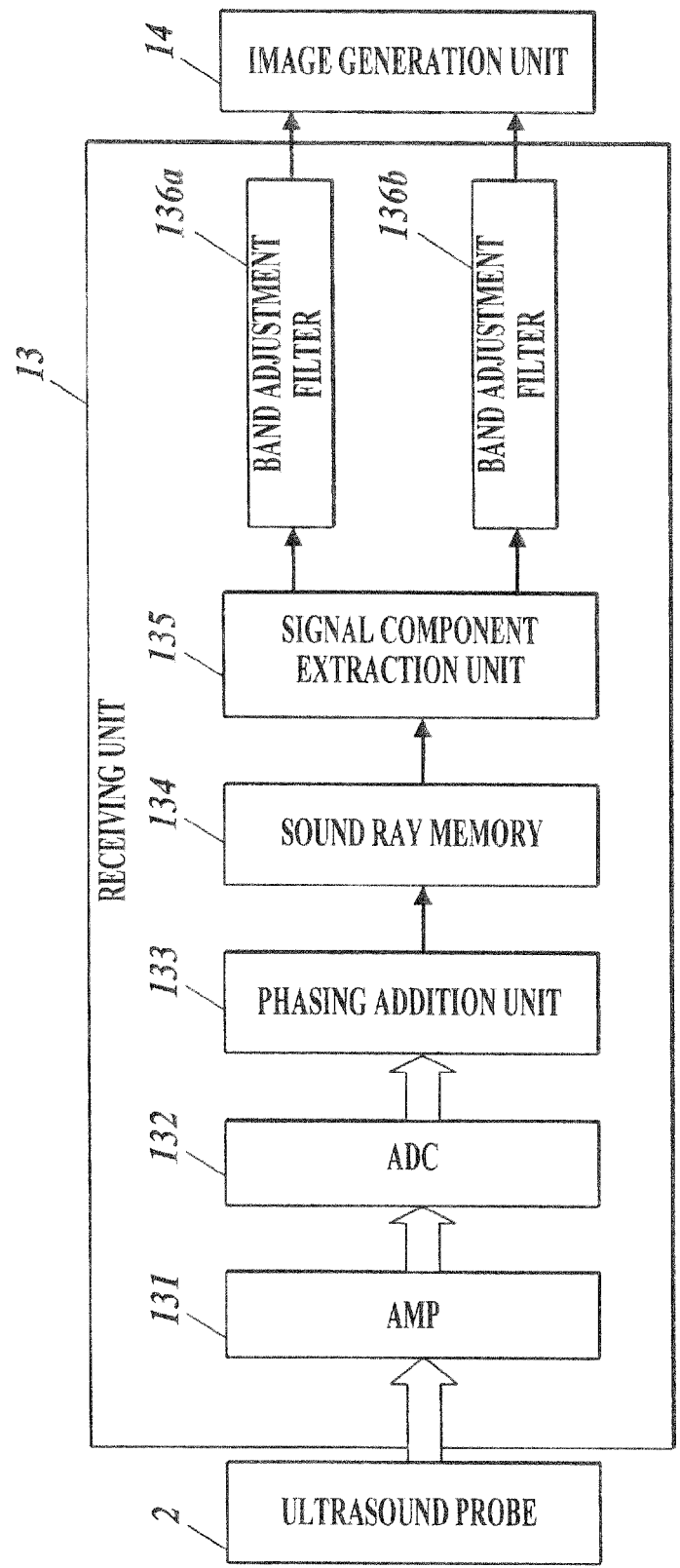
FIG. 20 is a block diagram showing a schematic configuration of a receiving unit according to the second embodiment.

As shown in FIG. 20, the receiving unit 13 of the ultrasound diagnostic imaging apparatus S in the second embodiment generates the third compound data and the fourth compound data by the signal component extracting unit 135 as described above in the first embodiment, performs the filter processing on the third compound data and the fourth compound data by the band adjustment filters 136a and 136b, respectively, and then, outputs the third compound data and the fourth compound data to the image generation unit 14.

Figure 21:
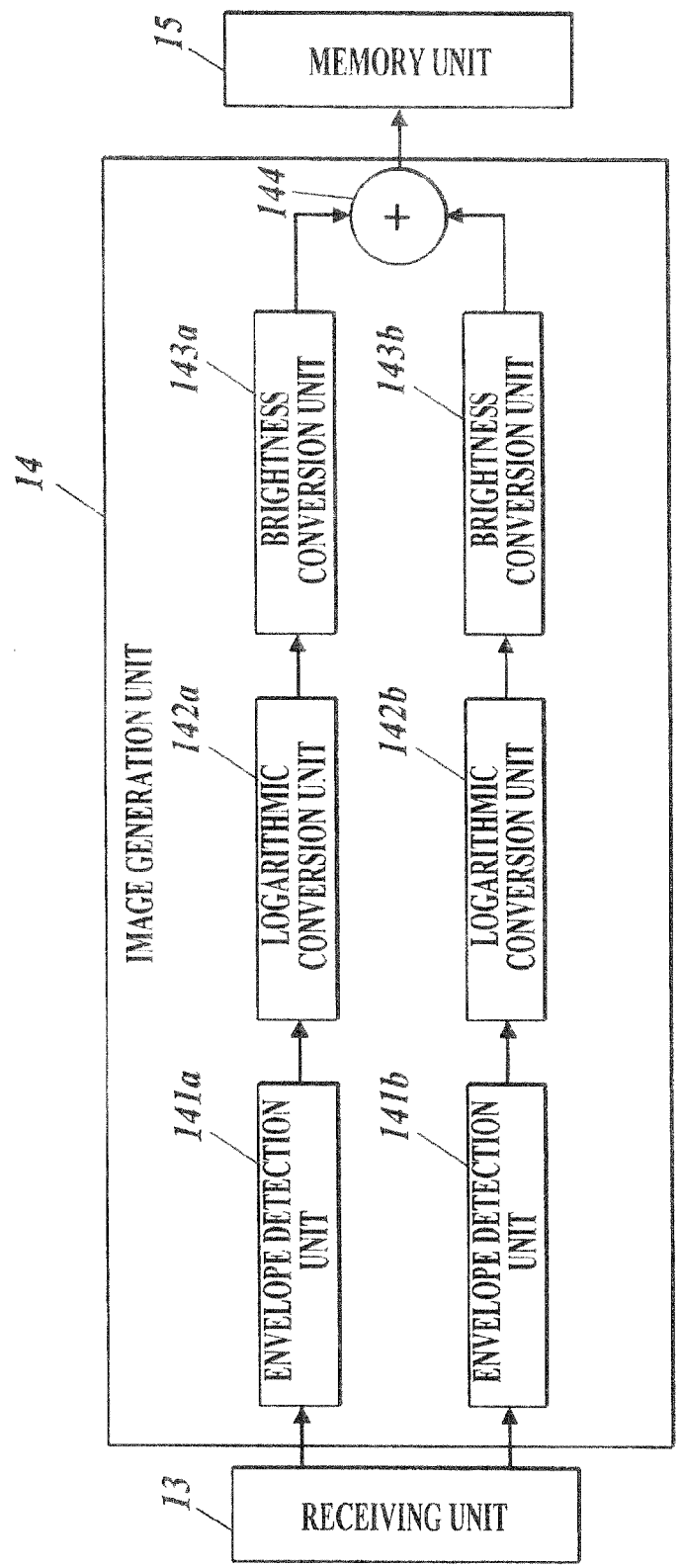
FIG. 21 is a block diagram showing a schematic configuration of an image generation unit according to the second embodiment.

As shown in FIG. 21, the image generation unit 14 performs conversion to envelope data by the envelope detection units 141a and 141b, logarithmic amplification by the logarithmic conversion units 142a and 142b and amplitude/brightness conversion by the brightness conversion units 143a and 143b on the third compound data and the fourth compound data, respectively, the third compound data and the fourth compound data being data of after the filter processing transmitted from the receiving unit 13. Thereafter, the image generation unit 14 adds the brightness data obtained from the third compound data and the brightness data obtained from the fourth compound data by the brightness data addition unit 144 to generate B-mode image data and outputs the generated B-mode image data to the memory unit 15. That is, the brightness data addition unit 144 performs the frequency compound processing on the brightness data obtained from the third compound data and the brightness data obtained from the fourth compound data to obtain the B-mode image data.

Figure 22:
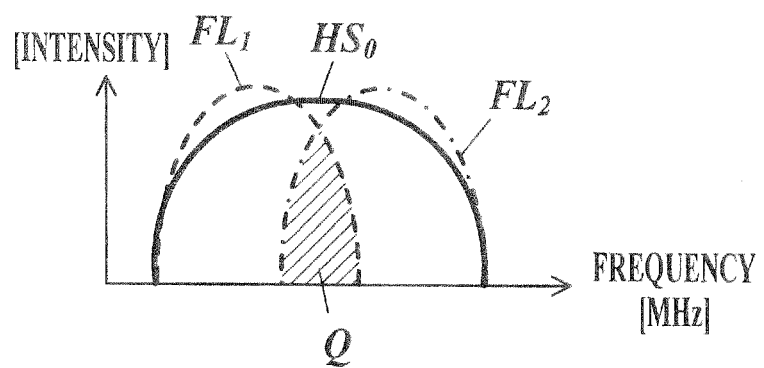
FIG. 22 is a diagram for explaining a conventional frequency compound method.
Figure 23:
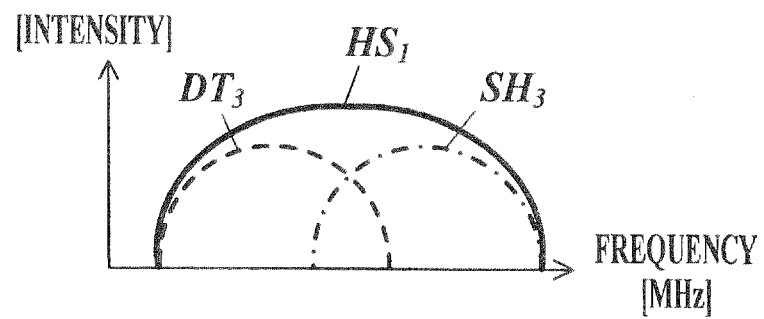
FIG. 23 is a diagram for explaining a frequency compound method according to the second embodiment.

Incidentally, as a method for controlling speckles, there can be considered a method where a received signal is separated into two signals formed of different frequency components and compounding the signals after performing the brightness conversion on each of the signals (frequency compound). Separation of received signal is carried out by the filter processing. At this time, there is know a method for setting the passing bands of filters so as not to overlap in order to improve the effect of the frequency compound processing. According to this method, the received signal which is subjected to the filter processing becomes narrow. As a result, degradation in resolution may occur. Further, as shown in FIG. 22, there is a method where the passing bands of the filters are set so as to overlap to a certain extent. According to such method, there is a problem that suppression effect of noises and the like is not brought out at the part Q where the passing bands $FL_1$ and $FL_2$ of a plurality of filters overlap although narrowing of the band $HS_0$ of harmonic component is suppressed. That is, in the conventional frequency compound method, it is difficult to realize both improvement in resolution and suppression of noise and the like because the second harmonic component and the difference frequency component cannot be separated by the filter processing in a region where the band of the second harmonic component and the band of the difference frequency component overlap.

In view of the above, in the embodiment, harmonic components can be separated while assuring no correlation between the second harmonic component $SH_3$ and the difference frequency component $DT_3$ where their generation processing are different essentially, and the frequency compound processing is performed on the basis of the separated harmonic components. Therefore, narrowing of the band $HS_1$ of harmonic component can be suppressed and an ultrasound image in which noise and the like are effectively suppressed ban be obtained without degradation in resolution.

As described above, according to the first and the second embodiments, the ultrasound probe 2 outputs ultrasound wave toward a subject due to a driving signal and also outputs a received signal by receiving the reflection ultrasound wave from the subject. The transmitting unit 12 outputs each of the first transmission signal, the second transmission signal which is a phase-inverted version of the signal waveform of the first transmission signal, the third transmission signal which is a time-inverted version of the signal waveform of the first transmission signal and the fourth transmission signal which is a phase-inverted and time-inverted version of the signal waveform of the first transmission signal as a driving signal and makes the ultrasound probe 2 generate transmission ultrasound wave. Here, the waveform of the first transmission signal is different from all of the waveforms of the third transmission signal and the fourth transmission signal. The signal component extraction unit 135 extracts second harmonic component and difference frequency component by compounding the first received signal obtained from the reflection ultrasound wave corresponding to the transmission ultrasound wave output from the ultrasound probe 2 due to the first transmission signal, the second received signal obtained from the reflection ultrasound wave corresponding to the transmission ultrasound wave output from the ultrasound probe 2 due to the second transmission signal, the third received signal obtained from the reflection ultrasound wave corresponding to the transmission ultrasound wave output from the ultrasound probe 2 due to the third transmission signal and the fourth received signal obtained from the reflection ultrasound wave corresponding to the transmission ultrasound wave output from the ultrasound probe 2 due to the fourth transmission signal. As a result, broadband harmonic component can be obtained by a transmission signal of square waveform which can output transmission ultrasound wave with a simple configuration and a good quality ultrasound image can be obtained. Further, because a plurality of types of harmonic components having different generation processes can be separated and extracted from received signals and they can be processed individually, the harmonic components can be controlled freely to generate a good quality ultrasound image data.

Further, according to the first embodiment, the phase adjustment filters 137a and 137b change the relative phase relation between the second harmonic component and the difference frequency component which are extracted by the signal component extraction unit 135. The signal adder 138 compounds the second harmonic component and the difference frequency component where the relative phase relation therebetween is changed by the phase adjustment filters 137a and 137b. The image generation unit 14 generates ultrasound image data of inside a subject on the basis of a received signal which is compound by the signal adder 138. As a result, because a broadband harmonic component can be made by operating the phases of plurality of types of harmonic compounds having different generation processes, a high quality ultrasound image of high resolution can be obtained.

Moreover, according to the first embodiment, the phase adjustment filters 137a and 137b set the changing amount of relative phase relation between the second harmonic component and the difference frequency component according to the depth of the reflection ultrasound wave received by the ultrasound probe 2. As a result, because phases can be operated taking the phase difference of the harmonic components which changes according to the depth into consideration, a high quality ultrasound image of high resolution can be obtained according to the depth.

Moreover, according to the second embodiment, the image generation unit 14 converts intensity of signals into the brightness data indicate the brightness of an image with respect to the second harmonic component and the difference frequency component extracted by the signal component extraction unit 135. The image generation unit 14 generates ultrasound image data of inside a subject by compounding the brightness data obtained by converting the second harmonic component and the brightness data obtained by converting the difference frequency component. As a result, an ultrasound image of broadband in which noise and speckle are effectively suppressed can be obtained.

Moreover, according to the first and the second embodiments, the signal component extraction unit 135 extracts the second harmonic component by obtaining the sum of the first received signal, the second received signal, the third received signal and the fourth received signal. The signal component extraction unit 135 extracts the difference frequency component by obtaining the difference between the sum of the first received signal and the second received signal and the sum of the third received signal and the fourth received signal. As a result, a plurality of harmonic components having different generation processes can be separated and extracted from received signals easily with a simple method.

Furthermore, according to the first and the second embodiments, the transmitting unit 12 outputs a driving signal in a form of a pulse signal of square waveform. As a result, production cost can be reduces due to being able to realized with a simple configuration.

Here, the descriptions of the embodiments of the present invention are examples of the ultrasound diagnostic imaging apparatus according to the present invention and the present invention is not limited to the descriptions. Detail configuration and detail operation of each functional unit constituting the ultrasound diagnostic imaging apparatus can also be changed arbitrarily.

Moreover, in the embodiment a second harmonic component and a difference frequency component are described as harmonic components included in received signals. However, third harmonic component and harmonic components thereafter may be included.

Furthermore, in the embodiment, the displacement amount of the phases of the second harmonic component and the difference frequency component is changed according to the depth of the reflection ultrasound received by the ultrasound probe 2. However, the displacement amount of the phases of the second harmonic component and the difference frequency component may be the same regardless of the depth.

Moreover, in the embodiment, the arithmetic method and arithmetic order for separating and extracting a second harmonic component and a difference frequency component from received signals may be different.

The entire disclosure of Japanese Patent Application No. 2011-261099 filed on Nov. 30, 2011 is incorporated herein by reference in its entirety.

What is claimed is:

1. An ultrasound diagnostic imaging apparatus comprising:
an ultrasound probe which comprises a transducer, wherein the transducer transmits a transmission ultrasound wave toward a subject in accordance with a driving signal, and the ultrasound probe outputs a received signal corresponding to a reflection ultrasound wave received by the transducer from the subject;

a transmitting unit which makes the ultrasound probe generate four transmission ultrasound waves by outputting, as the driving signal, each of a first transmission signal, a second transmission signal which is a phase-inverted version of a signal waveform of the first transmission signal, a third transmission signal which is a time-inverted version of the signal waveform of the first transmission signal, and a fourth transmission signal which is a phase-inverted and time-inverted version of the signal waveform of the first transmission signal, wherein the waveform of the first transmission signal is different from waveforms of the third transmission signal and the fourth transmission signal, and each of the four transmission ultrasound waves includes a first fundamental component and a second fundamental component, a frequency of the second fundamental component being different from a frequency of the first fundamental component;

a signal component extraction unit which extracts a second harmonic component and a difference frequency component having a frequency which is a difference between the first fundamental component and the second fundamental component, from a harmonic component generated due to transmission of the four transmission ultrasound waves, and separates the second harmonic component and the difference frequency component from each other, wherein the signal component extraction unit extracts the second harmonic component such that the second harmonic component is separated from the difference frequency component by obtaining a sum of all of (i) a first received signal obtained from a reflection ultrasound wave corresponding to the transmission ultrasound wave output from the ultrasound probe due to the first transmission signal, (ii) a second received signal obtained from a reflection ultrasound wave corresponding to the transmission ultrasound wave output from the ultrasound probe due to the second transmission signal, (iii) a third received signal obtained from a reflection ultrasound wave corresponding to the transmission ultrasound wave output from the ultrasound probe due to the third transmission signal, and (iv) a fourth received signal obtained from a reflection ultrasound wave corresponding to the transmission ultrasound wave output from the ultrasound probe due to the fourth transmission signal, and extracts the difference frequency component such that the difference frequency component is separated from the second harmonic component by obtaining a difference between (i) a sum of the first received signal and the second received signal and (ii) a sum of the third received signal and the fourth received signal;

a phase changing unit which changes a relative phase relation between the second harmonic component and the difference frequency component extracted and separated by the signal component extraction unit;

a signal compounding unit which compounds the second harmonic component and the difference frequency component, wherein the relative phase relation is changed by the phase changing unit; and an image generation unit which generates ultrasound image data of inside the subject based on a received signal compounded by the signal compounding unit.

2. The ultrasound diagnostic imaging apparatus of claim 1, wherein the phase changing unit sets a changing amount of the relative phase relation between the second harmonic component and the difference frequency component according to a depth of the reflection ultrasound wave which is received by the ultrasound probe.

3. The ultrasound diagnostic imaging apparatus of claim 1, wherein the transmitting unit outputs the driving signal in a form of a pulse signal of a square wave.

4. An ultrasound diagnostic imaging apparatus comprising:

an ultrasound probe which comprises a transducer, wherein the transducer transmits a transmission ultrasound wave toward a subject in accordance with a driving signal, and the ultrasound probe outputs a received signal corresponding to a reflection ultrasound wave received by the transducer from the subject;

a transmitting unit which makes the ultrasound probe generate four transmission ultrasound waves by outputting, as the driving signal, each of a first transmission signal, a second transmission signal which is a phase-inverted version of a signal waveform of the first transmission signal, a third transmission signal which is a time-inverted version of the signal waveform of the first transmission signal, and a fourth transmission signal which is a phase-inverted and time-inverted version of the signal waveform of the first transmission signal, wherein the waveform of the first transmission signal is different from waveforms of the third transmission signal and the fourth transmission signal, and each of the four transmission ultrasound waves includes a first fundamental component and a second fundamental component, a frequency of the second fundamental component being different from a frequency of the first fundamental component;

a signal component extraction unit which extracts a second harmonic component and a difference frequency component having a frequency which is a difference between the first fundamental component and the second fundamental component, from a harmonic component generated due to transmission of the four transmission ultrasound waves, and separates the second harmonic component and the difference frequency component from each other, wherein the signal component extraction unit extracts the second harmonic component such that the second harmonic component is separated from the difference frequency component by obtaining a sum of all of (i) a first received signal obtained from a reflection ultrasound wave corresponding to the transmission ultrasound wave output from the ultrasound probe due to the first transmission signal, (ii) a second received signal obtained from a reflection ultrasound wave corresponding to the transmission ultrasound wave output from the ultrasound probe due to the second transmission signal, (iii) a third received signal obtained from a reflection ultrasound wave corresponding to the transmission ultrasound wave output from the ultrasound probe due to the third transmission signal, and (iv) a fourth received signal obtained from a reflection ultrasound wave corresponding to the transmission ultrasound wave output from the ultrasound probe due to the fourth transmission signal, and extracts the difference frequency component such that the difference frequency component is separated from the second harmonic component by obtaining a difference between (i) a sum of the first received signal and the second received signal and (ii) a sum of the third received signal and the fourth received signal; and an image generation unit which converts each of the second harmonic component and the difference frequency component extracted and separated by the signal component extraction unit into brightness data in which intensity of a signal is indicated in terms of a brightness of an image and generates ultrasound image data of inside the subject by compounding the brightness data obtained by converting the second harmonic component and the brightness data obtained by converting the difference frequency component.

\* \* \* \* \*